(12) United States Patent
Dunkel et al.

(10) Patent No.: US 7,745,483 B2
(45) Date of Patent: *Jun. 29, 2010

(54) 2-HALOFURYL-THIENYL-3-CARBOXAMIDES

(75) Inventors: Ralf Dunkel, Lyons (FR); Hans-Ludwig Elbe, Wuppertal (DE); Jörg Nico Greul, Leichlingen (DE); Benoit Hartmann, Langenfeld (DE); Peter Dahmen, Neuss (DE); Karl-Heinz Kuck, Langenfeld (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 226 days.

This patent is subject to a terminal disclaimer.

(21) Appl. No.: 10/588,293

(22) PCT Filed: Jan. 22, 2005

(86) PCT No.: PCT/EP2005/000629

§ 371 (c)(1),
(2), (4) Date: May 16, 2007

(87) PCT Pub. No.: WO2005/075452

PCT Pub. Date: Aug. 18, 2005

(65) Prior Publication Data

US 2008/0064874 A1    Mar. 13, 2008

(30) Foreign Application Priority Data

Feb. 6, 2004    (DE)    ........................ 10 2004 005 785

(51) Int. Cl.
*A01N 43/06* (2006.01)

(52) U.S. Cl. .................. 514/448; 514/461; 549/72; 549/73; 549/483; 549/487; 549/504

(58) Field of Classification Search ................ 514/448, 514/461; 549/72, 73, 483, 487, 504

See application file for complete search history.

(56) References Cited

U.S. PATENT DOCUMENTS

| | | | |
|---|---|---|---|
| 7,176,228 B2 * | 2/2007 | Elbe et al. .................... | 514/406 |
| 7,208,169 B2 | 4/2007 | Dunkel et al. | |
| 7,314,958 B2 | 1/2008 | Elbe et al. | |
| 2004/0204470 A1 | 10/2004 | Elbe et al. | |
| 2007/0191454 A1 | 8/2007 | Dunkel et al. | |
| 2007/0203148 A1 | 8/2007 | Dunkel et al. | |
| 2008/0085924 A1 | 4/2008 | Dunkel et al. | |
| 2009/0076113 A1 | 3/2009 | Dunkel et al. | |

FOREIGN PATENT DOCUMENTS

| | | |
|---|---|---|
| WO | WO 02/08197 A1 | 1/2002 |
| WO | WO 03/010149 A1 | 2/2003 |
| WO | WO 2004/005242 A1 | 1/2004 |
| WO | WO 2005/004606 A2 | 1/2005 |

OTHER PUBLICATIONS

Patent Abstracts of Japan, English language abstract of Japanese Publication No. 01-313402, published Dec. 18, 1989.
Patent Abstracts of Japan, English language abstract of Japanese Publication No. 02-040374, published Feb. 9, 1990.
Patent Abstracts of Japan, English language abstract of Japanese Publication No. 02-178259, published Jul. 11, 1990.
Patent Abstracts of Japan, English language abstract of Japanese Publication No. 08-176112, published Jul. 9, 1996.
Patent Abstracts of Japan, English language abstract of Japanese Publication No. 2001-0302605, published Oct. 31, 2001.
Dialog File 351, Accession No. 12361222, WPI English language abstract of WO 2002/08197.
Dialog File 351, Accession No. 13194256, WPI English language abstract of WO 2003/010149.
Dialog File 351, Accession No. 13989121, WPI English language abstract of WO 2004/005242.
Office Action for U.S. Appl. No. 10/579,033, Dunkel et al., mailed Jul. 22, 2008.
Office Action for U.S. Appl. No. 10/579,033, Dunkel et al., mailed Dec. 10, 2008.
International Search Report for International Application No. PCT/EP05/00629, European Patent Office, Netherlands, mailed on Jun. 6, 2005.
Office Action for U.S. Appl. No. 10/512,706, Dunkel et al., mailed May 17, 2006.
Office Action for U.S. Appl. No. 12/097,753, Dunkel et al., mailed December 23, 3009.

* cited by examiner

*Primary Examiner*—Kamal A Saeed
*Assistant Examiner*—Valerie Rodriguez-Garcia
(74) *Attorney, Agent, or Firm*—Sterne, Kessler, Goldstein & Fox P.L.L.C

(57) ABSTRACT

Novel 2-halofuryl/thienyl-3-carboxamides of the formula (I)

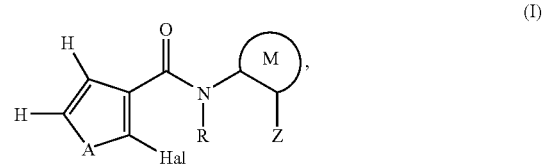

in which
A, Hal, R, M and Z are as defined in the description,
a plurality of processes for preparing these compounds and their use for controlling unwanted microorganisms, and also novel intermediates and their preparation.

12 Claims, No Drawings

2-HALOFURYL-THIENYL-3-CARBOXAMIDES

The present invention relates to novel 2-halofuryl/thienyl-3-carboxamides, to a plurality of processes for their preparation and to their use for controlling unwanted microorganisms.

It is already known that numerous carboxamides have fungicidal properties (cf., for example, EP-A 0 737 682, EP-A 0 591 699, EP-A 0 589 301, EP-A 0 545 099, DE-A24 09 011, DE-A 20 06 472, JP-A 2001-302605, JP-A 10-251240, JP-A 8-176112, JP-A 8-92223 and JP-A 53-72823). Thus, numerous furyl/thienyl-3-carboxamides whose furyl/thienyl ring is substituted in the 2-position by methyl or trifluoromethyl are already known. The only carboxamides substituted by halogen in the 2-position of the heterocycle are 2,5-dichloro-N-{3'-[(methoxyimino)methyl]biphenyl-2-yl}thiophene-3-carboxamide and 2,5-dichloro-N-{4'-[(methoxyimino)methyl]biphenyl-2-yl}thiophene-3-carboxamide (cf. WO 02/08197). The activity of these compounds is good; however, in some cases, for example at low application rates, it is unsatisfactory.

2-Halofuryl/thienyl-3-carboxamides, whose furyl/thienyl ring carries, in addition to the halogen substituent, no further substituents are novel.

This invention now provides novel 2-halofuryl/thienyl-3-carboxamides of the formula (I)

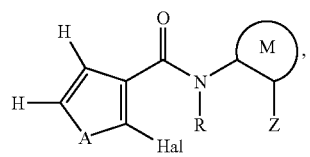

in which

A represents O (oxygen) or S (sulphur),

Hal represents halogen,

R represents hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-$C_1$-$C_3$-alkyl)carbonyl-$C_1$-$C_3$-alkyl, halo-$C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)R$^1$, —CONR$^2$R$^3$ or —CH$_2$NR$^4$R$^5$, R$^1$ represents hydrogen, $C_1$-$C_8$-alkyl, $C_1$-$C_8$-alkoxy, $C_1$-$C_4$-alkoxy-$C_1$-$C_4$-alkyl. $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine- and/or bromine atoms, R$^2$ and R$^3$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine- and/or bromine atoms, R$^2$ and R$^3$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain one or two further non-adjacent heteroatoms from the group consisting of oxygen, sulphur and NR$^6$, R$^4$ and R$^5$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, R$^4$ and R$^5$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and NR$^6$, R$^6$ represents hydrogen or $C_1$-$C_6$-alkyl, M represents a phenyl, thiophene, pyridine, pyrimidine, pyridazine or pyrazine ring, each of which is monosubstituted by R$^7$, or represents a thiazole ring substituted by R$^{7-A}$, R$^7$ represents hydrogen, fluorine, chlorine, methyl, isopropyl, methylthio or trifluoromethyl, R$^{7-A}$ represents hydrogen, methyl, methylthio or trifluoromethyl, Z represents Z$^1$, Z$^2$, Z$^3$ or Z$^4$, in which Z$^1$ represents phenyl which is optionally mono- to penta-substituted by identical or different substituents, Z$^2$ represents bicycloalkyl or cycloalkyl which is optionally mono- or polysubstituted by identical or different substituents, Z$^3$ represents unsubstituted $C_2$-$C_{20}$-alkyl or represents $C_1$-$C_{20}$-alkyl which is mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —SiR$^8$R$^9$R$^{10}$ and $C_3$-$C_6$-cycloalkyl, where the cycloalkyl moiety for its part may optionally be mono- or polysubstituted by identical or different substituents from the group consisting of halogen and $C_1$-$C_4$-alkyl, Z$^4$ represents $C_2$-$C_{20}$-alkenyl or $C_2$-$C_{20}$-alkynyl, each of which is optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halo-dialkylamino, —SiR$^8$R$^9$R$^{10}$ and $C_3$-$C_6$-cycloalkyl, where the cycloalkyl moiety for its part may optionally be mono- or polysubstituted by identical or different substituents from the group consisting of halogen and $C_1$-$C_4$-alkyl, R$^8$ and R$^9$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, R$^{10}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or represents in each case optionally substituted phenyl or phenylalkyl, or M and Z together represent 1H-2,3-dihydroinden-4-yl, 1,3-dihydro-2-benzofuran-4-yl or 1,3-dihydro-2-benzothien-4-yl, each of which is optionally mono- to trisubstituted by methyl.

Furthermore, it has been found that 2-halofuryl/thienyl-3-carboxamides of the formula (I) are obtained when a) carboxylic acid derivatives of the formula (II)

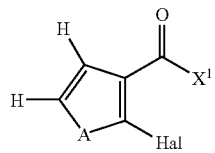

(II)

in which

A and Hal are as defined above and $X^1$ represents halogen or hydroxyl are reacted with aniline derivatives of the formula (III)

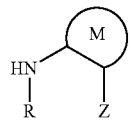

(III)

in which R, M and Z are as defined above, if appropriate in the presence of a catalyst, if appropriate in the presence of a condensing agent, if appropriate in the presence of an acid binder and if appropriate in the presence of a diluent, or b) halocarboxamides of the formula (IV)

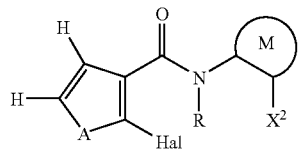

(IV)

in which

A, Hal, R and M are as defined above, $X^2$ represents bromine, iodine or trifluoromethylsulphonate, are reacted with boronic acid derivatives of the formula (V)

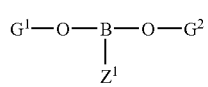

(V)

in which $Z^1$ is as defined above and $G^1$ and $G^2$ each represent hydrogen or together represent tetramethylethylene, in the presence of a catalyst, if appropriate in the presence of an acid binder and if appropriate in the presence of a diluent, or c) boronic acid derivatives of the formula (VI)

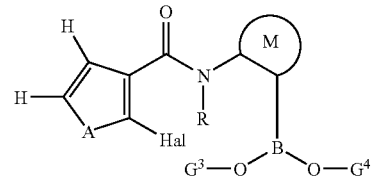

(VI)

in which

A, Hal, R and M are as defined above, $G^3$ and $G^4$ each represent hydrogen or together represent tetramethylethylene are reacted with phenyl derivatives of the formula (VII)

$$X^3—Z^1$$ (VII)

in which $Z^1$ is as defined above and $X^3$ represents chlorine, bromine, iodine or trifluoromethylsulphonate, if appropriate in the presence of a catalyst, if appropriate in the presence of an acid binder and if appropriate in the presence of a diluent, or d) halocarboxamides of the formula (IV)

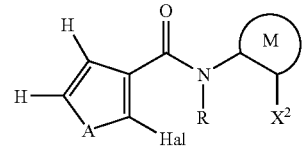

(IV)

in which

A, Hal, R and M are as defined above, $X^2$ represents bromine, iodine or trifluoromethylsulphonate, are reacted with phenyl derivatives of the formula (VII)

$$X^3—Z^1$$ (VII)

in which $Z^1$ is as defined above and $X^3$ represents chlorine, bromine, iodine or trifluoromethylsulphonate, in the presence of a palladium or nickel catalyst and in the presence of 4,4,4',4',5,5,5',5'-octamethyl-2,2'-bis-1,3,2-dioxaborolane, if appropriate in the presence of an acid binder and if appropriate in the presence of a diluent, or e) 2-halofuryl/thienyl-3-carboxamides of the formula (I-a)

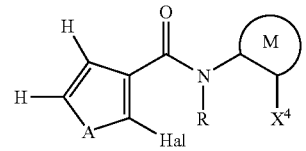

(I-a)

in which

A, Hal, R and M are as defined above, $X^4$ represents $C_2$-$C_{20}$-alkenyl or $C_2$-$C_{20}$-alkynyl which are in each case optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and /or $C_3$-$C_6$-cycloalkyl, where the cycloalkyl moiety for its part may optionally be substituted by halogen and/or $C_1$-$C_4$ alkyl, are hydrogenated, if appropriate in the presence of a diluent and if appropriate in the presence of a catalyst, or f) hydroxyalkylcarboxamides of the formula (VIII)

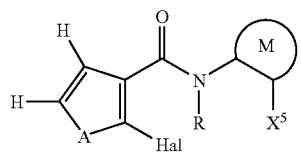

(VIII)

in which

A, Hal, R and M are as defined above, $X^5$ represents $C_2$-$C_{20}$-hydroxyalkyl which is optionally additionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and $C_3$-$C_6$-cycloalkyl, where the cycloalkyl moiety for its part may optionally be substituted by halogen and/or $C_1$-$C_4$-alkyl, are dehydrated, if appropriate in the presence of a diluent and if appropriate in the presence of an acid, or g) halocarboxamides of the formula (IV)

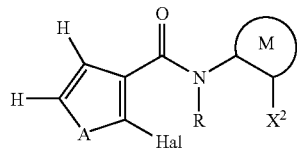

(IV)

in which

A, Hal, R and M are as defined above, $X^2$ represents bromine, iodine or trifluoromethylsulphonate, are reacted with an alkyne of the formula (IX)

(IX)

in which $G^5$ represents $C_2$-$C_{18}$-alkyl which is optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and $C_3$-$C_6$-cycloalkyl, where the cycloalkyl moiety for its part may optionally be substituted by halogen and/or $C_1$-$C_4$-alkyl, or an alkene of the formula (X)

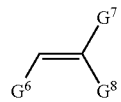

(X)

in which $G^6$, $G^7$ and $G^8$ independently of one another each represent hydrogen or alkyl which is optionally mono- or polysubstituted by identical or different substituents from the group consisting of halogen, alkylthio, alkylsulphinyl, alkylsulphonyl; alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and $C_3$-$C_6$-cycloalkyl, where the cycloalkyl moiety for its part may optionally be substituted by halogen and/or $C_1$-$C_4$-alkyl and the total number of carbon atoms of the open-chain molecular moiety (without substituents) does not exceed the number 20, if appropriate in the presence of a diluent, if appropriate in the presence of an acid binder and if appropriate in the presence of one or more catalysts, or h) ketones of the formula (XI)

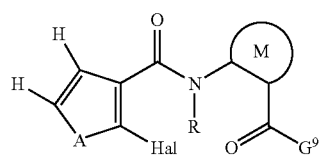

(XI)

in which

A, Hal, R and M are as defined above, $G^9$ represents hydrogen or $C_1$-$C_{18}$-alkyl which is optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and $C_3$-$C_6$-cycloalkyl, where the cycloalkyl moiety for its part may optionally be substituted by halogen and/or $C_1$-$C_4$-alkyl, are reacted with a phosphorus compound of the general formula (XII)

(XII)

in which $G^{10}$ represents $C_1$-$C_{18}$-alkyl which is optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and/or $C_3$-$C_6$-cycloalkyl, where the cycloalkyl moiety for its part may optionally be substituted by halogen and/or $C_1$-$C_4$-alkyl, Px represents a grouping —$P^+(C_6H_5)_3Cl^-$, —$P^+(C_6H_5)_3Br^-$, —$P^+(C_6H_5)_3\ I^-$, —$P(=O)(OCH_3)_3$ or —$P(=O)(OC_2H_5)_3$, if appropriate in the presence of a diluent, or i) 2-halofuryl/thienyl-3-carboxamides of the formula (I-b)

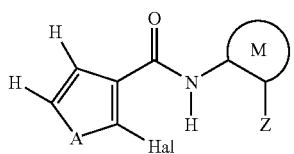

(I-b)

in which
A, Hal, R, M and Z are as defined above
are reacted with halides of the formula (XIII)

$$R^a\text{—}X^6 \qquad (XIII)$$

in which
$R^a$ represents $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^1$, —CONR$^2$R$^3$ or —CH$_2$NR$^4$R$^5$, $R^1$, $R^2$, $R^3$, $R^4$ and $R^5$ are as defined above,
$X^6$ represents chlorine, bromine or iodine,
in the presence of a base and in the presence of a diluent.

Finally, it has been found that the novel 2-halofuryl/thienyl-3-carboxamides of the formula (I) have very good microbicidal properties and can be used for controlling unwanted microorganisms both in crop protection and in the protection of materials.

Surprisingly, the 2-halofuryl/thienyl-3-carboxamides of the formula (I) have considerably better fungicidal activity than the constitutionally most similar active compounds of the prior art having the same direction of action.

The compounds according to the invention may, if appropriate, be present as mixtures of different possible isomeric forms, in particular of stereoisomers, such as, for example, E and Z, threo and erythro and also optical isomers, and, if appropriate, also of tautomers. What is claimed are both the E and the Z and the threo and erythro and also the optical isomers, any mixtures of these isomers and also the possible tautomeric forms.

The formula (I) provides a general definition of the 2-halofuryl/thienyl-3-carboxamides according to the invention. Preferred radical definitions of the formulae given above and below are stated below. These definitions apply both to the end products of the formula (I) and, correspondingly, to all intermediates.

A preferably represents O (oxygen).
A furthermore preferably represents S (sulphur).
Hal preferably represents fluorine, chlorine, bromine or iodine.

Hal particularly preferably represents chlorine, bromine or iodine.
Hal very particularly preferably represents iodine.
R preferably represents hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13, fluorine, chlorine and/or bromine atoms;

($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)$R^1$, —CONR$^2$R$^3$ or —CH$_2$NR$^4$R$^5$.

R particularly preferably represents hydrogen, methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH$_2$(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^1$, —CONR$^2$R$^3$ or —CH$_2$NR$^4$R$^5$.

R very particularly preferably represents hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

$R^1$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^1$ particularly preferably represents hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

R² and R³ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

R² and R³ furthermore together with the nitrogen atom to which they are attached preferably represent a saturated heterocycle having 5 or 6 ring atoms which is optionally mono- to tetrasubstituted by identical or different substituents from the group consisting of halogen and $C_1$-$C_4$-alkyl, where the heterocycle may contain 1 or 2 further non-adjacent heteroatoms from the group consisting of oxygen, sulphur and $NR^6$.

R² and R³ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

R² and R³ furthermore together with the nitrogen atom to which they are attached particularly preferably form a saturated heterocycle from the group consisting of morpholine, thiomorpholine and piperazine, which heterocycle is optionally mono- to tetrasubstituted by identical or different substituents from the group consisting of fluorine, chlorine, bromine and methyl, where the piperazine may be substituted on the second nitrogen atom by $R^6$.

R⁴ and R⁵ independently of one another preferably represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms.

R⁴ and R⁵ furthermore together with the nitrogen atom to which they are attached preferably form a saturated heterocycle having 5 or 6 ring atoms which is optionally mono- or polysubstituted by identical or different substituents from a group consisting of halogen and $C_1$-$C_4$-alkyl, where the heterocycle may contain 1 or 2 further non-adjacent heteroatoms from the group consisting of oxygen, sulphur and $NR^6$.

R⁴ and R⁵ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

R⁴ and R⁵ furthermore together with the nitrogen atom to which they are attached particularly preferably represent a saturated heterocycle from the group consisting of morpholine, thiomorpholine and piperazine, which heterocycle is optionally mono- to tetrasubstituted by identical or different substituents from the group consisting of fluorine, chlorine, bromine and methyl, where the piperazine may be substituted on the second nitrogen atom by $R^6$.

R⁶ preferably represents hydrogen or $C_1$-$C_4$-alkyl.

R⁶ particularly preferably represents hydrogen, methyl, ethyl, n- or isopropyl, n-, iso-, sec- or tert-butyl.

M preferably represents one of the cycles below

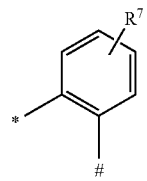
M-1

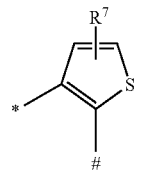
M-2

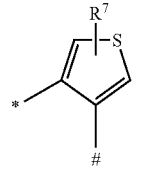
M-3

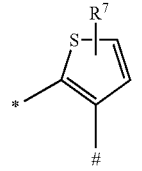
M-4

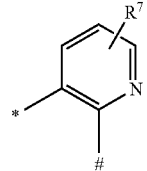
M-5

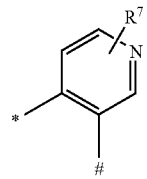
M-6

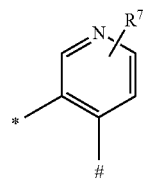
M-7

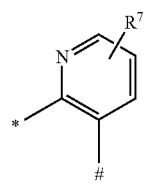
M-8

-continued

M-9

[chemical structure]

M-10

[chemical structure]

M-11

[chemical structure]

M-12

[chemical structure]

M-13

[chemical structure]

M-14

[chemical structure]

where the bond marked "*" is attached to the amide and the bond marked "#" is attached to the radical Z.

M particularly preferably represents a cycle selected from the group consisting of M-1, M-2, M-3, M4, M-5, M-6, M-9, M-10 and M-11.

M very particularly preferably represents a cycle selected from the group consisting of M-1, M-2, M-5, M-6, M-9, M-10 and M-11.

M especially preferably represents the cycle M-1.

M furthermore especially preferably represents the heterocycle M-2.

M furthermore especially preferably represents the heterocycle M-5.

M furthermore especially preferably represents the heterocycle M-6.

M furthermore especially preferably represents the heterocycle M-9.

M furthermore especially preferably represents the heterocycle M-10.

M furthermore especially preferably represents the heterocycle M-11.

$R^7$ preferably represents hydrogen.

$R^7$ furthermore, if M represents M-1, preferably represents fluorine,. where fluorine, is particularly preferably located in the 4-, 5- or 6-position, very particularly preferably in the 4- or 6-position, especially in the 4-position, of the anilide radical [cf. formula (I) above].

$R^7$ furthermore, if M represents M-1, preferably represents chlorine, where chlorine is particularly preferably located in the 5-position of the anilide radical [cf. formula (I) above].

$R^7$ furthermore, if M represents M-1, preferably represents methyl, where methyl is particularly preferably located in the 3-position of the anilide radical [cf. formula (I) above].

$R^7$ furthermore, if M represents M-1, preferably represents trifluoromethyl, where trifluoromethyl is particularly preferably located in the 4- or 5-position of the anilide radical [cf. formula (I) above].

$R^7$ furthermore, if M represents M-2, M-3 or M-4, preferably represents chlorine, where chlorine is particularly preferably located in the 5-position (M-2, M-3) or in the 3-position (M-4).

$R^7$ furthermore, if M represents M-2, M-3 or M-4, preferably represents methyl, where methyl is particularly preferably located in the 5-position (M-2, M-3) or in the 3-position (M-4).

$R^7$ furthermore, if M represents M-5, M-6, M-7 or M-8, preferably represents fluorine, where fluorine, is particularly preferably located in the 6-position (M-5, M-6) or in the 3-position (M-7, M-8).

$R^7$ furthermore, if M represents M-5, M-6, M-7 or M-8, preferably represents chlorine, where chlorine is particularly preferably located in the 6-position (M-5, M-6) or in the 3-position (M-7, M-8).

$R^7$ furthermore, if M represents M-5, M-6, M-7 or M-8, preferably represents methyl, where methyl is particularly preferably located in the 4-position (M-5) or in the 3-position (M-6, M-7, M-8).

$R^7$ furthermore, if M represents M-9, preferably represents methyl, where methyl is particularly preferably located in the 3-position.

$R^7$ furthermore, if M represents M-9, preferably represents trifluoromethyl, where trifluoromethyl is particularly preferably located in the 3-position.

$R^7$ furthermore, if M represents M-12, preferably represents methyl, where methyl is particularly preferably located in the 4-position.

$R^7$ furthermore, if M represents M-12, preferably represents trifluoromethyl, where trifluoromethyl is particularly preferably located in the 4-position.

$R^7$ furthermore, if M represents M-13, preferably represents methyl, where methyl is particularly preferably located in the 3-position.

$R^7$ furthermore, if M represents M-13, preferably represents trifluoromethyl, where trifluoromethyl is particularly preferably located in the 3-position.

$R^7$ furthermore, if M represents M-14, preferably represents methyl, where methyl is particularly preferably located in the 3-position.

$R^7$ furthermore, if M represents M-14, preferably represents trifluoromethyl, where trifluoromethyl is particularly preferably located in the 3-position.

$R^{7-A}$ preferably represents hydrogen.

$R^{7-A}$ furthermore preferably represents methyl.

$R^{7-A}$ furthermore preferably represents trifluoromethyl.

Z preferably represents $Z^1$.

$Z^1$ preferably represents phenyl which is optionally mono- to pentasubstituted by identical or different substituents, the substituents in each case being selected from the list $W^1$.

$Z^1$ particularly preferably represents monosubstituted phenyl, the substituents in each case being selected from the list $W^1$.

$Z^1$ also particularly preferably represents phenyl which is disubstituted by identical or different substituents, the substituents in each case being selected from the list $W^1$.

$Z^1$ also particularly preferably represents phenyl which is trisubstituted by identical or different substituents, the substituents in each case being selected from the list $W^1$.

$Z^1$ very particularly preferably represents phenyl which is monosubstituted in the 4-position, the substituents in each case being selected from the list $W^1$.

$Z^1$ very particularly preferably represents phenyl which is disubstituted by identical or different substituents in the 3,4-position, the substituents in each case being selected from the list $W^1$.

$Z^1$ very particularly preferably represents phenyl which is disubstituted by identical or different substituents in the 2,3-position, the substituents in each case being selected from the list $W^1$.

$Z^1$ very particularly preferably represents phenyl which is disubstituted by identical or different substituents in the 2,4-position, the substituents in each case being selected from the list $W^1$.

$Z^1$ very particularly preferably represents phenyl which is disubstituted by identical or different substituents in the 3,5-position, the substituents in each case being selected from the list $W^1$.

$Z^1$ very particularly preferably represents phenyl which is trisubstituted by identical or different substituents in the 2,4,6-position, the substituents in each case being selected from the list $W^1$.

$W^1$ represents halogen, cyano, nitro, amino, hydroxyl, formyl, carboxyl, carbamoyl, thiocarbamoyl;

in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy having 1 to 6 carbon atoms in the respective hydrocarbon chains, alkenylcarbonyl or alkynylcarbonyl, having 2 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, oxo, methyl, trifluoromethyl and ethyl;

or the grouping $-C(Q^1)=N-Q^2$, in which $Q^1$ represents hydrogen, hydroxyl or alkyl having 1 to 4 carbon atoms, haloalkyl having 1 to 4 carbon atoms and 1 to 9 fluorine, chlorine and/or bromine atoms or cycloalkyl having 1 to 6 carbon atoms and $Q^2$ represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkynyloxy having in each case 2 to 4 carbon atoms, and also phenyl, phenoxy, phenylthio, benzoyl, benzoylethenyl, cinnamoyl, heterocyclyl or phenylalkyl, phenylalkyloxy, phenylalkylthio, or heterocyclylalkyl, having in each case 1 to 3 carbon atoms in the respective alkyl chains, each of which radicals is optionally mono- to trisubstituted in the cyclic moiety by halogen and/or straight-chain or branched alkyl or alkoxy having 1 to 4 carbon atoms.

$W^1$ preferably represents fluorine, chlorine, bromine, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, in each case doubly attached difluoromethylenedioxy or tetrafluoroethylenedioxy, or the grouping $-C(Q^1)=N-Q^2$, in which $Q^1$ represents hydrogen, methyl, ethyl or trifluoromethyl and $Q^2$ represents hydroxy, methoxy, ethoxy, propoxy or isopropoxy.

Z also preferably represents $Z^2$.

$Z^2$ preferably represents cycloalkyl or bicycloalkyl having in each case 3 to 10 carbon atoms and being in each case optionally mono- to tetrasubstituted by identical or different substituents from the group consisting of halogen and $C_1$-$C_4$-alkyl.

$Z^2$ particularly preferably represents cyclopropyl, cyclopentyl, cyclohexyl, cycloheptyl, cyclooctyl, cyclononyl, bicyclo[2.2.1]heptyl or bicyclo[2.2.2]octyl, each of which is optionally mono- to tetrasubstituted by identical or different substituents from the group consisting of chlorine and methyl.

$Z^2$ very particularly preferably represents chlorine- and methyl-substituted cyclopropyl.

Z also preferably represents $Z^3$.

$Z^3$ preferably represents unsubstituted $C_2$-$C_{20}$-alkyl or represents $C_1$-$C_{20}$-alkyl which is mono- or polysubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, $-SiR^8R^9R^{10}$ and $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and $C_1$-$C_4$-haloalkyl.

$Z^3$ particularly preferably represents unsubstituted $C_2$-$C_{20}$-alkyl.

$Z^3$ also particularly preferably represents $C_1$-$C_{20}$-alkyl which is substituted by fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^8R^9R^{10}$, cyclopropyl, dichlorocyclopropyl, cyclobutyl, cyclopentyl or cyclohexyl; very particularly preferably represents $C_1$-$C_{20}$-alkyl which is substituted by fluorine, chlorine, methylthio, ethylthio, n- or isopropylthio, n-, iso-, sec-, tert-butylthio, pentylthio, hexylthio, methylsulphonyl, ethylsulphonyl, n- or isopropylsulphonyl, n-, iso-, sec-, tert-butylsulphonyl, methoxy, ethoxy, n- or isopropoxy, n-, iso-, sec-, tert-butoxy, methylamino, ethylamino, n- or isopropylamino, n-, iso-, sec-, tert-butylamino, dimethylamino, diisopropylamino, trifluoromethylthio, trifluoromethoxy, —$SiR^8R^9R^{10}$, cyclopropyl, dichlorocyclopropyl, cyclobutyl, cyclopentyl or cyclohexyl.

Z also preferably represents $Z^4$.

$Z^4$ preferably represents $C_2$-$C_{20}$-alkenyl or $C_2$-$C_{20}$-alkynyl, each of which is optionally mono- or polysubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and $C_1$-$C_4$-haloalkyl.

$Z^4$ particularly preferably represents $C_2$-$C_{20}$-alkyl or $C_2$-$C_{20}$-alkynyl, each of which is optionally substituted by fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^8R^9R^{10}$, cyclopropyl, dichlorocyclopropyl, cyclobutyl, cyclopentyl or cyclohexyl.

$Z^4$ very particularly preferably represents $C_2$-$C_{20}$-alkenyl or $C_2$-$C_{20}$-alkynyl.

$R^8$ and $R^9$ independently of one another preferably represent $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl.

$R^8$ and $R^9$ independently of one another particularly preferably represent methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

$R^8$ and $R^9$ independently of one another very particularly preferably represent methyl, methoxy, methoxymethyl or methylthiomethyl.

$R^8$ and $R^9$ especially preferably each represent methyl.

$R^{10}$ preferably represents $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

$R^{10}$ particularly preferably represents methyl, ethyl, n- or isopropyl, n-, sec-, iso- or tert-butyl, methoxy, ethoxy, n- or isopropoxy, n-, sec-, iso- or tert-butoxy, methoxymethyl, ethoxymethyl, methoxyethyl, ethoxyethyl, methylthiomethyl, ethylthiomethyl, methylthioethyl, ethylthioethyl, cyclopropyl, phenyl or benzyl.

$R^{10}$ very particularly preferably represents methyl, ethyl, n- or isopropyl, iso- or tert-butyl, methoxy, isopropoxy, iso- or tert-butoxy, methoxymethyl, methylthiomethyl or phenyl.

$R^{10}$ especially preferably represents methyl, ethyl, n- or isopropyl, iso- or tert-butyl, methoxy, iso-propoxy, iso- or tert-butoxy.

$R^{10}$ most preferably represents methyl.

M and Z also preferably together represent 1,1,3-trimethyl-1H-2,3-dihydroinden-4-yl, 1,3-dimethyl-1H-2,3-dihydroinden-4-yl, 1,1,3-trimethyl-1,3-dihydro-2-benzofuran-4-yl, 1,3-dimethyl-1,3-dihydro-2-benzofuran-4-yl, 1,1,3-trimethyl-1,3-dihydro-2-benzothien-4-yl or 1,3-dimethyl-1,3-dihydro-2-benzothien-4-yl.

M and Z also particularly preferably together represent 1,1,3-trimethyl-1H-2,3-dihydroinden-4-yl.

Preference is given to those compounds of the formula (I), in which all radicals each have the preferred meanings mentioned above.

Particular preference is given to those compounds of the formula (I) in which all radicals have in each case the particularly preferred meanings mentioned above.

Preferred, and in each case to be understood as being a subgroup of the compounds of the formula (I) mentioned above, are the following groups of novel carboxamides:

Group 1: 2-Halofuryl/thienyl-3-carboxamides of the formula (I-b)

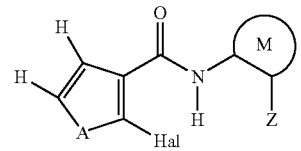

in which A, Hal, R, M and Z are as defined above.

Group 2: 2-Halofuryl/thienyl-3-carboxamides of the formula (I-c)

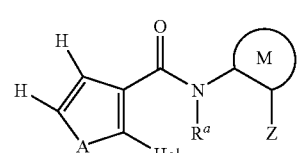

(I-c)

in which A, Hal, $R^a$, M and Z are as defined above.

$R^a$ preferably represents $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy) carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)$R^1$, —$CONR^2R^3$ or —$CH_2NR^4R^5$.

$R^a$ particularly preferably represents methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —CH$_2$N—CHO, —CH$_2$O—CH$_3$, —CH$_2$CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)R$^1$, —CONR$^2$R$^3$ or —CH$_2$NR$^4$R$^5$.

$R^a$ very particularly preferably represents methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

Group 3: 2-Halofuryl/thienyl-3-carboxamides of the formula (I-d)

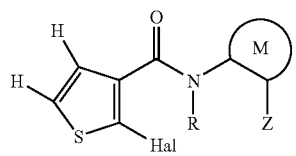

in which Hal, R, M and Z are as defined above.

Group 4: 2-Halofuryl/thienyl-3-carboxamides of the formula (I-e)

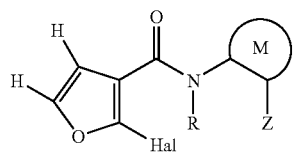

in which Hal, R, M and Z are as defined above.

Group 5: 2-Halofuryl/thienyl-3-carboxamides of the formula (I-f)

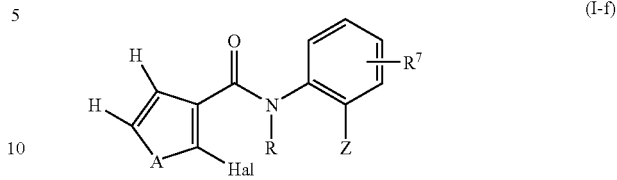

in which A, Hal, R, R$^7$ and Z are as defined above.

Preference is given to compounds of the formula (I-f), in which A represents S (sulphur).

Preference is furthermore given to compounds of the formula (I-f), in which A represents O (oxygen).

Group 6: 2-Halofuryl/thienyl-3-carboxamides of the formula (I-g)

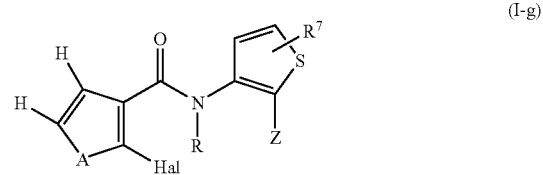

in which A, Hal, R, R$^7$ and Z are as defined above.

Preference is given to compounds of the formula (I-g), in which A represents S (sulphur).

Preference is furthermore given to compounds of the formula (I-g), in which A represents O (oxygen).

Group 7: 2-Halofuryl/thienyl-3-carboxamides of the formula (I-h)

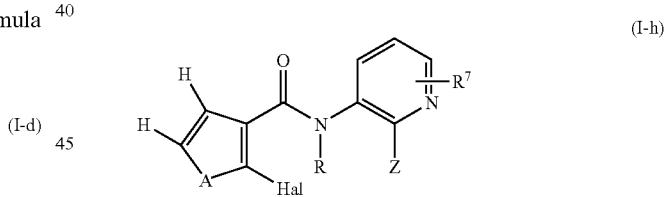

in which A, Hal, R, R$^7$ and Z are as defined above.

Preference is given to compounds of the formula (I-h), in which A represents S (sulphur).

Preference is furthermore given to compounds of the formula (I-h), in which A represents O (oxygen).

Group 8: 2-Halofuryl/thienyl-3-carboxamides of the formula (I-i)

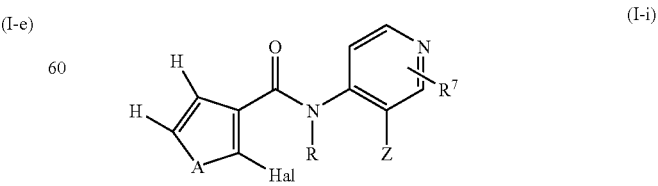

in which A, Hal, R, R$^7$ and Z are as defined above.

Preference is given to compounds of the formula (I-i), in which A represents S (sulphur).

Preference is furthermore given to compounds of the formula (I-i), in which A represents O (oxygen).

Group 9: 2-Halofuryl/thienyl-3-carboxamides of the formula (I-j)

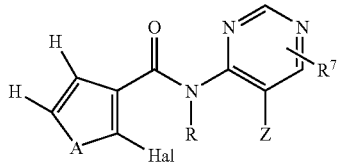

(I-j)

in which A, Hal, R, R⁷ and Z are as defined above.

Preference is given to compounds of the formula (I-j), in which A represents S (sulphur).

Preference is furthermore given to compounds of the formula (I-j), in which A represents O (oxygen).

Group 10: 2-Halofuryl/thienyl-3-carboxamides of the formula (I-k)

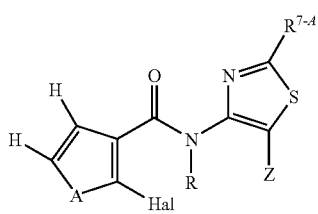

(I-k)

in which A, Hal, R, R⁷ and Z are as defined above.

Preference is given to compounds of the formula (I-k), in which A represents S (sulphur).

Preference is furthermore given to compounds of the formula (I-k), in which A represents O (oxygen).

Group 11: 2-Halofuryl/thienyl-3-carboxamides of the formula (I-l)

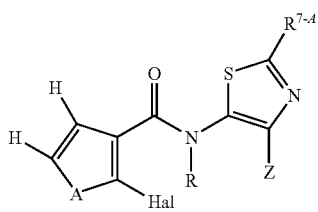

(I-l)

in which A, Hal, R, R⁷ and Z are as defined above.

Preference is given to compounds of the formula (I-l), in which A represents S (sulphur).

Preference is furthermore given to compounds of the formula (I-l), in which A represents O (oxygen).

Group 12: 2-Halofuryl/thienyl-3-carboxamides of the formula (I-m)

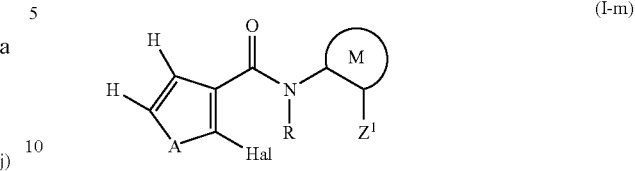

(I-m)

in which A, Hal, R, M and $Z^1$ are as defined above.

Preference is given to compounds of the formula (I-m), in which A represents S (sulphur).

Preference is furthermore given to compounds of the formula (I-m), in which A represents O (oxygen).

Group 13: 2-Halofuryl/thienyl-3-carboxamides of the formula (I-n)

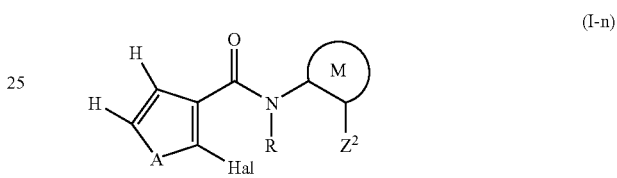

(I-n)

in which A, Hal, R, M and $Z^2$ are as defined above.

Preference is given to compounds of the formula (I-n), in which A represents S (sulphur).

Preference is furthermore given to compounds of the formula (I-n), in which A represents O (oxygen).

Group 14: 2-Halofuryl/thienyl-3-carboxamides of the formula (I-o)

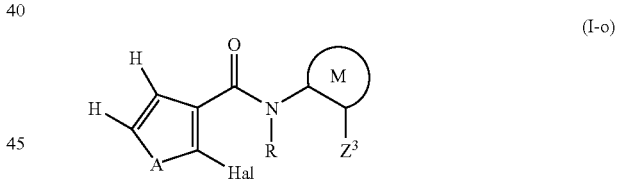

(I-o)

in which A, Hal, R, M and $Z^3$ are as defined above.

Preference is given to compounds of the formula (I-o), in which A represents S (sulphur).

Preference is furthermore given to compounds of the formula (I-o), in which A represents O (oxygen).

Group 15: 2-Halofuryl/thienyl-3-carboxamides of the formula (I-p)

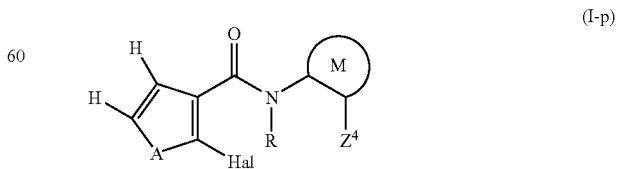

(I-p)

in which A, Hal, R, M and $Z^4$ are as defined above.

Preference is given to compounds of the formula (I-p), in which A represents S (sulphur).

Preference is furthermore given to compounds of the formula (I-p), in which A represents O (oxygen).

Group 16: 2-Halofuryl/thienyl-3-carboxamides of the formula (I-q)

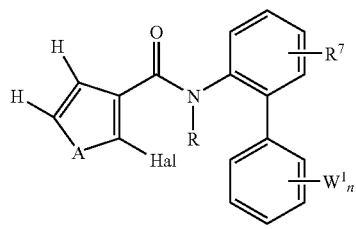

(I-q)

in which A, Hal, R, R$^7$ and W$^1$ are as defined above and n represents 0, 1, 2, 3, 4 or 5, where the substituents W$^1$ can be identical or different if n represents 2, 3, 4 or 5.

Preference is given to compounds of the formula (I-q), in which A represents S (sulphur).

Preference is furthermore given to compounds of the formula (I-q), in which A represents O (oxygen).

Group 17: 2-Halofuryl/thienyl-3-carboxamides of the formula (I-r)

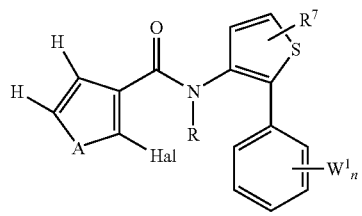

(I-r)

in which A, Hal, R, R$^7$ and W$^1$ are as defined above and n represents 0, 1, 2, 3, 4 or 5, where the substituents W$^1$ can be identical or different if n represents 2, 3, 4 or 5.

Preference is given to compounds of the formula (I-r), in which A represents S (sulphur).

Preference is furthermore given to compounds of the formula (I-r), in which A represents O (oxygen).

Group 18: 2-Halofuryl/thienyl-3-carboxamides of the formula (I-s)

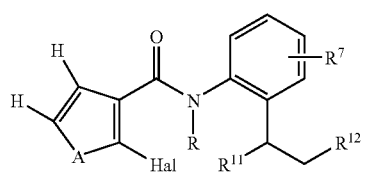

(I-s)

in which
A, Hal, R and R$^7$ are as defined above,
R$^{11}$ represents hydrogen or methyl,
R$^{12}$ represents —SiR$^8$R$^9$R$^{10}$, where R$^8$, R$^9$ and R$^{10}$ are as defined above, or represents —CR$^{13}$R$^{14}$R$^{15}$, where R$^{13}$ represents fluorine, chlorine, bromine, iodine, C$_1$-C$_4$-alkylthio, C$_1$-C$_4$-alkylsulphinyl, C$_1$-C$_4$-alkylsulphonyl, C$_1$-C$_4$-alkoxy, C$_1$-C$_4$-alkylamino, di(C$_1$-C$_4$-alkyl)amino, C$_1$-C$_4$-haloalkyl, C$_1$-C$_4$-haloalkylthio, C$_1$-C$_4$-haloalkylsulphinyl, C$_1$-C$_4$-haloalkylsulphonyl, C$_1$-C$_4$-haloalkoxy, C$_1$-C$_4$-haloalkylamino or halo-di(C$_1$-C$_4$-alkyl)amino, and R$^{14}$ and R$^{15}$ independently of one another represent hydrogen, fluorine, chlorine, bromine, iodine, C$_1$-C$_4$-alkylthio, C$_1$-C$_4$-alkylsulphinyl, C$_1$-C$_4$-alkylsulphonyl, C$_1$-C$_4$-alkoxy, C$_1$-C$_4$-alkylamino, di(C$_1$-C$_4$-alkyl)amino, C$_1$-C$_4$-haloalkylthio, C$_1$C$_4$-haloalkylsulphinyl, C$_1$-C$_4$-haloalkylsulphonyl, C$_1$-C$_4$-haloalkoxy, C$_1$-C$_4$-haloalkylamino or halo-di(C$_1$-C$_4$-alkyl)amino.

Preference is given to the compounds of the formula (I-s), in which A represents S (sulphur).

Preference is furthermore given to compounds of the formula (I-s) in which A represents O (oxygen).

Group 19: 2-Halofuryl/thienyl-3-carboxamides of the formula (I-t)

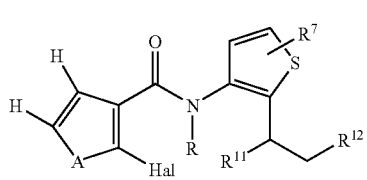

(I-t)

in which
A, Hal, R and R$^7$ are as defined above,
R$^{11}$ represents hydrogen or methyl,
R$^{12}$ represents —SiR$^8$R$^9$R$^{10}$, where R$^8$, R$^9$ and R$^{10}$ are as defined above, or represents —CR$^{13}$R$^{14}$R$^{15}$, where R$^{13}$ represents fluorine, chlorine, bromine, iodine, C$_1$-C$_4$-alkylthio, C$_1$-C$_4$-alkylsulphinyl, C$_1$-C$_4$-alkylsulphonyl, C$_1$-C$_4$-alkoxy, C$_1$-C$_4$-alkylamino, di(C$_1$-C$_4$-alkyl)amino, C$_1$-C$_4$-haloalkyl, C$_1$-C$_4$-haloalkylthio, C$_1$-C$_4$-haloalkylsulphinyl, C$_1$-C$_4$-haloalkylsulphonyl, C$_1$-C$_4$-haloalkoxy, C$_1$-C$_4$-haloalkylamino or halo-di(C$_1$-C$_4$-alkyl)amino, and R$^{14}$ and R$^{15}$ independently of one another represent hydrogen, fluorine, chlorine, bromine, iodine, C$_1$-C$_4$-alkylthio, C$_1$-C$_4$-alkylsulphinyl, C$_1$-C$_4$-alkylsulphonyl, C$_1$-C$_4$-alkoxy, C$_1$-C$_4$-alkylamino, di(C$_1$-C$_4$-alkyl)amino, C$_1$-C$_4$-haloalkylthio, C$_1$-C$_4$-haloalkylsulphinyl, C$_1$-C$_4$-haloalkylsulphonyl, C$_1$-C$_4$-haloalkoxy, C$_1$-C$_4$-haloalkylamino or halo-di(C$_1$-C$_4$-alkyl)amino.

Preference is given to the compounds of the formula (I-t), in which A represents S (sulphur).

Preference is furthermore given to compounds of the formula (I-t) in which A represents O (oxygen).

Most preferred are compounds of the formula (I) (and also of groups 1 to 19) in which R represents hydrogen.

Most preferred are compounds of the formula (I) (and also of groups 1 to 19) in which R represents formyl.

Most preferred are furthermore compounds of the formula (I) (and also of groups 1 to 19), in which R represents —C(=O)C(=O)R$^1$, where R$^1$ is as defined above.

Saturated or unsaturated hydrocarbon chains, such as alkyl or alkenyl, can in each case be straight-chain or branched as far as this is possible, including in combination with heteroatoms, such as, for example, in alkoxy.

The definition C$_1$-C$_{20}$-alkyl is the largest range for an alkyl radical defined here. Specifically, this definition comprises the meanings methyl, ethyl, n-, isopropyl, n-, iso-, sec-, tert-butyl and in each case all isomeric pentyls, hexyls, heptyls, octyls, nonyls, decyls, undecyls, dodecyls, tridecyls, tetradecyls, pentadecyls, hexadecyls, heptadecyls, octadecyls, nonadecyls and eicosyls. A preferred range is $C_2$-$C_{12}$-alkyl, such as ethyl and straight-chain or branched propyl, butyl, pentyl, hexyl, heptyl, octyl, nonyl, decyl, undecyl and dodecyl, in particular straight-chain or branched $C_3$-$C_{10}$-alkyl, such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-methylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl, 2,6-dimethyl-4-heptyl and 1-methyl-2-cyclopropylethyl.

Halogen-substituted alkyl represents, for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

The substituent —$SiR^8R^9R^{10}$ preferably represents the following radicals: $SiMe_3$, $SiMe_2Et$, $SiMe_2CHMe_2$, $SiMe_2CH_2CHMe_2$, $SiMe_2CH_2CMe_3$, $SiMe_2OCHMe_2$, $SiMe_2OCH_2CHMe_2$, $SiMe_2OMe$, $SiMe_2CMe_3$, $SiMe_2CH_2CH_2Me$.

The definition $C_2$-$C_{20}$-alkenyl is the largest range for an alkenyl radical defined here. Specifically, this definition comprises the meanings ethenyl, n-, isopropenyl, n-, iso-, sec-, tert-butenyl, and in each case all isomeric pentenyls, hexenyls, heptenyls, octenyls, nonenyls, decenyls, undecenyls, dodecenyls, tridecenyls, tetradecenyls, pentadecenyls, hexadecenyls, heptadecenyls, octadecenyls, nonadecenyls and eicosenyls, 1-methyl-1-propenyl, 1-ethyl-1-butenyl, 2,4-dimethyl-1-pentenyl, 2,4-dimethyl-2-pentenyl.

The definition $C_2$-$C_{20}$-alkynyl is the largest range for an alkynyl radical defined here. Specifically, this definition comprises the meanings ethynyl, n-, isopropynyl, n-, iso-, sec-, tert-butynyl, and in each case all isomeric pentynyls, hexynyls, heptynyls, octynyls, nonynyls, decynyls, undecynyls, dodecynyls, tridecynyls, tetradecynyls, pentadecynyls, hexadecynyls, heptadecynyls, octadecynyls, nonadecynyls and eicosynyls.

Optionally substituted radicals can be mono- or polysubstituted, where in the case of polysubstitutions the substituents may be identical or different. Thus, the definition dialkylamino also includes an amino group which is asymmetrically substituted by alkyl, such as, for example, methylethylamino.

Halogen-substituted radicals, such as, for example, haloalkyl, are mono- or polyhalogenated. In the case of polyhalogenation, the halogen atoms can be identical or different. Here, halogen represents fluorine, chlorine, bromine and iodine, in particular fluorine, chlorine and bromine.

The general or preferred radical definitions or illustrations given above can be combined between the respective ranges and preferred ranges as desired. They apply both to the end products and, correspondingly, to precursors and intermediates. In particular, the compounds mentioned in groups 1 to 18 can be combined both with the general and with preferred, particularly preferred, etc. meanings, and here, too, any combinations between the preferred ranges are possible. For example, the radicals Hal and Z in the formula (I-d) can have the general meanings, whereas R has the preferred meanings and M the particularly preferred meanings.

Illustration of the Processes and Intermediates:

Process (a)

Using 2-iodothiophene-3-carbonyl chloride and 3',4'-dichloro-1,1'-biphenyl-2-amine as starting materials, the course of the process (a) according to the invention can be illustrated by the formula scheme below.

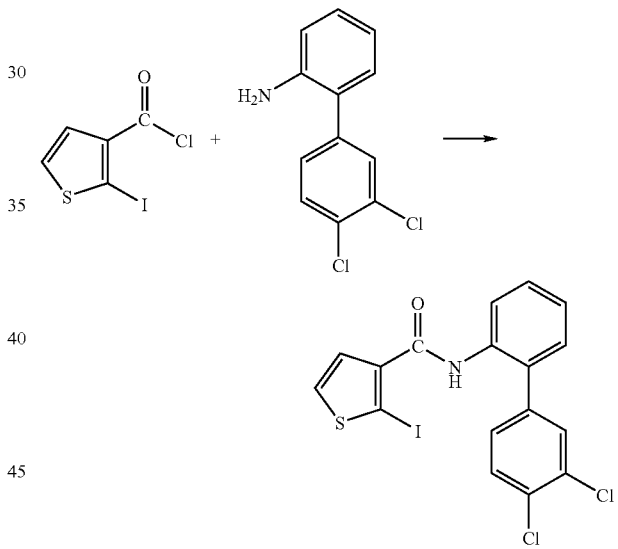

Formula (II) provides a general definition of the carboxylic acid derivatives required as starting materials for carrying out the process (a) according to the invention. In this formula (II), A and Hal preferably, particularly preferably and very particularly preferably have those meanings which have already been mentioned in connection with the description of the compounds of the formula (I) according to the invention as being preferred, particularly preferred and very particularly preferred, respectively, for these radicals. $X^1$ preferably represents chlorine or hydroxyl.

Using 2-iodthiophene-3-carboxylic acid and 3',4'-dichloro-1,1'-biphenyl-2-amine as starting materials in the presence of coupling agents, such as, for example, dicyclohexylcarbodiimide, or generating the acid halide in situ, for example using PyBrop (bromo-tris-pyrrolidinophosphonium hexafluorophosphate) or oxalyl chloride, the course of the process (a) according to the invention can be illustrated by the formula scheme below.

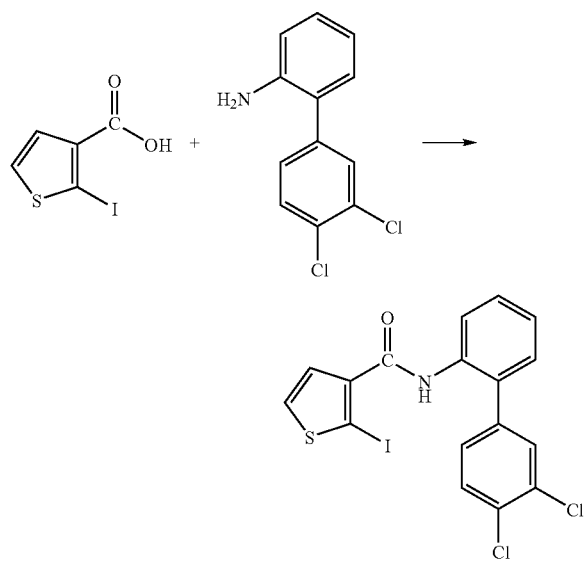

The carboxylic acid derivatives of the formula (II) are known and/or can be prepared by known processes (Heterocycles 1993, 36, 1867).

The formula (III) provides a general definition of the aniline derivatives furthermore required as starting materials for carrying out the process (a) according to the invention. In this formula (III), R, M and Z preferably, particularly preferably and very particularly preferably have those meanings which have already been mentioned in connection with the description of the compounds of the formula (I) according to the invention as being preferred, particularly preferred and very particularly preferred, respectively, for these radicals.

Most of the starting materials of the formula (III) are known, and/or they can be prepared by known processes (cf., for example, Bull. Korean Chem. Soc. 2000, 21, 165-166; Chem. Pharm. Bull. 1992, 40, 240-244; Heterocycles 1989, 29, 1013-1016; J. Med. Chem. 1996, 39, 892-903; Synthesis 1995, 713-16; Synth. Commun. 1994, 24, 267-272; Synthesis 1994, 142-144; DE-A 27 27 416; EP-A 0 824 099; EP-A 0 737 682, WO 93/11117, WO 03/080628; EP-A 0 545 099, EP-A 0 589 301, EP-A 0 589 313 and WO 02/38542).

It is also possible to prepare, initially, aniline derivatives of the formula (III-a)

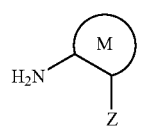

(III-a)

in which M and Z are as defined above and then to react these, if appropriate, with halides of the formula (XIII)

 (XIII)

in which $R^a$ and $X^6$ are as defined above, in the presence of a base and in the presence of a diluent. [The reaction conditions of the process (i) according to the invention apply correspondingly.]

Aniline derivatives of the formula (III-b)

in which

M is as defined above and $Z^{3-A}$ represents $C_1$-$C_{20}$-alkyl which is monosubstituted by alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, are chained, for example, according to scheme 1 below:

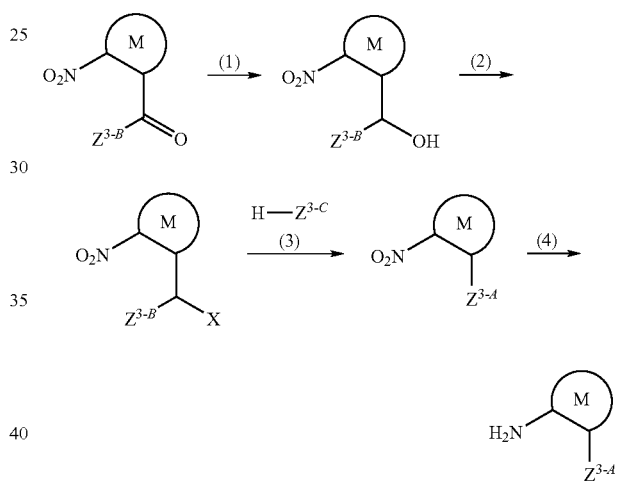

In this scheme 1, $Z^{3-A}$ is as defined above. $Z^{3-B}$ represents unsubstituted $C_2$-$C_{20}$-alkyl, $Z^{3-C}$ represents alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino or halodialkylamino. X represents chlorine, bromine or iodine. The preferred ranges given for $Z^3$ apply correspondingly to the meanings featured here.

Aniline derivatives of the formula (III-c)

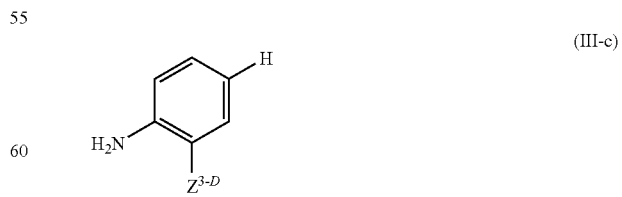

in which $Z^{3-D}$ represents $C_1$-$C_{20}$-alkyl which is mono- or polysubstituted by halogen, are obtained, for example, according to scheme 2 below:

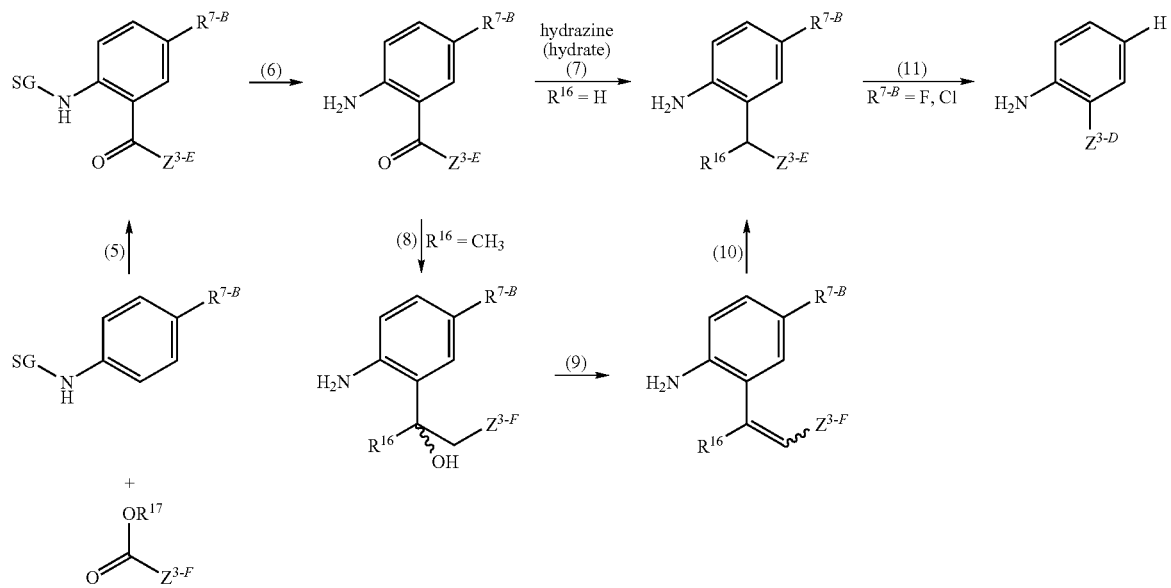

In this scheme 2, $Z^{3-D}$ is as defined above. $Z^{3-B}$ represents $C_1$-$C_{19}$-alkyl which is mono- or polysubstituted by halogen. $Z^{3-F}$ represents $C_1$-$C_{17}$-alkyl which is mono- or polysubstituted by halogen. $R^{7-B}$ represents fluorine, chlorine, methyl, isopropyl, methylthio or trifluoromethyl. $R^{16}$ represents hydrogen or methyl. SG represents a protective group, preferably Piv (tert-butylcarbonyl), Boc (tert-butoxycarbonyl-), Cbz (benzyloxycarbonyl-), trifluoroacetyl-, Fmoc (9-fluorenylmethoxy-carbonyl-) or Troc (2,2,2-trichloroethoxycarbonyl-). $R^{17}$ represents $C_1$-$C_4$-alkyl, preferably methyl or ethyl.

The preferred ranges given for $Z^3$ and $R^7$ apply correspondingly to the meanings featured here.

Process (b)

Using N-(2-bromophenyl)-2-iodothiophene-3-carboxamide and 3,4-dichlorophenyl boronic acid as starting materials and a catalyst, the course of the process (b) according to the invention can be illustrated by the formula scheme below.

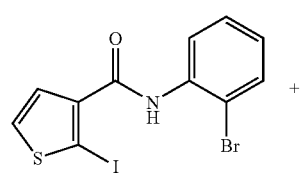

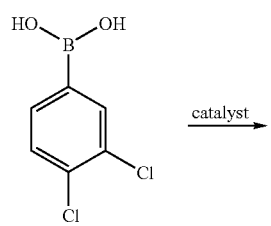

-continued

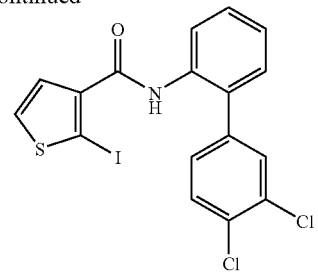

The formula (IV) provides a general definition of the halocarboxamides required as starting materials for carrying out the process (b) according to the invention. In this formula (IV), A, Hal, R and M preferably, particularly preferably and very particularly preferably have those meanings which have already been mentioned in connection with the description of the compounds of the formula (I) according to the invention as being preferred, particularly preferred and very particularly preferred, respectively, for these radicals. $X^2$ represents bromine or iodine.

The halocarboxamides of the formula (IV) have hitherto not been disclosed. As novel chemical compounds, they also form part of the subject-matter of the present application. They are obtained when j) Carboxylic acid derivatives of the formula (II)

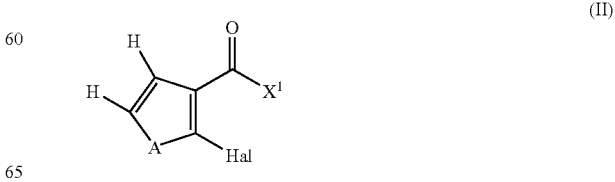

in which A, Hal and $X^1$ are as defined above, are reacted with haloanilines of the formula (XIV),

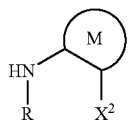
(XIV)

in which R, M and $X^2$ are as defined above,
if appropriate in the presence of a catalyst, if appropriate in the presence of a condensing agent, if appropriate in the presence of an acid binder and if appropriate in the presence of a diluent.

The carboxylic acid derivatives of the formula (II) required as starting materials for carrying out the process (j) according to the invention have already been described in connection with the process (a) according to the invention.

The formula (XIV) provides a general definition of the haloanilines furthermore required as starting materials for carrying out the process (j) according to the invention. In this formula (XIV), R, M and $X^2$ preferably, particularly preferably and very particularly preferably have those meanings which have already been mentioned in connection with the description of the compounds of the formula (I) according to the invention or of the precursors of the formula (III) as being preferred, particularly preferred and very particularly preferred, respectively, for these radicals.

The haloanilines of the formula (XIV) are commercially available chemicals for synthesis or can be obtained by known processes.

It is also possible to prepare, initially, haloanilines of the formula (XIV-a)

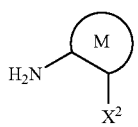
(XIV-a)

in which M and $X^2$ are as defined above and then to react these, if appropriate, with halides of the formula (XIII)

— (XIII)

$R^a$—$X^6$ (XIII)

in which $R^a$ and $X^6$ are as defined above, in the presence of a base and in the presence of a diluent. [The reaction conditions of the process (i) according to the invention apply correspondingly.]

The formula (V) provides a general definition of the boronic acid derivatives furthermore required as starting materials for carrying out the process (b) according to the invention. In this formula (V), $Z^1$ preferably, particularly preferably and very particularly preferably has those meanings which have already been mentioned in connection with the description of the compounds of the formula (I) according to the invention as being preferred, particularly preferred and very particularly preferred, respectively, for $Z^1$. $G^1$ and $G^2$ each represent hydrogen or together represent tetramethylethylene.

The boronic acid derivatives of the formula (V) are known and/or can be prepared by known processes (cf., for example, WO 01/90084 and U.S. Pat. No. 5,633,218).

Process c)

Using (2-{[(2-iodo-3-thienyl)carbonyl]amino}phenyl)boronic acid and 4-bromo-1,2-dichlorobenzene as starting materials and a catalyst, the course of the process (c) according to the invention can be illustrated by the formula scheme below.

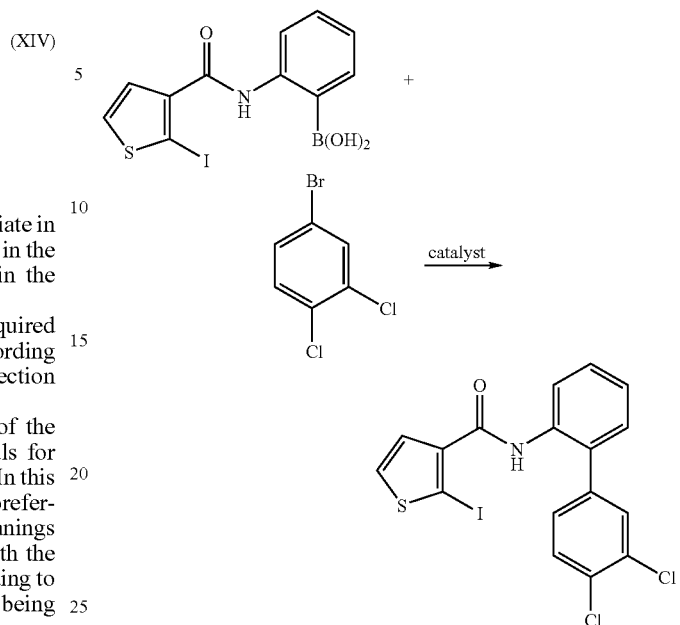

The formula (VI) provides a general definition of the boronic acid derivatives required as starting materials for carrying out the process (c) according to the invention. In this formula (VI), A, Hal, R and M preferably, particularly preferably and very particularly preferably have those meanings which have already been mentioned in connection with the description of the compounds of the formula (I) according to the invention as being preferred, particularly preferred and very particularly preferred, respectively, for these radicals. $G^3$ and $G^4$ each represent hydrogen or together represent tetramethylethylene.

The boronic acid derivatives of the formula (VI) have hitherto not been disclosed. They are novel chemical compounds and also form part of the subject-matter of the present application. They are obtained when k) a carboxylic acid derivative of the formula (II)

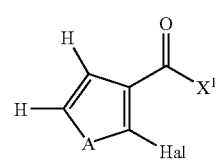
(II)

in which A, Hal and $X^2$ are as defined above, is reacted with an anilineboronic acid derivative of the formula (XV)

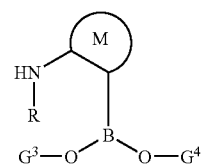
(XV)

in which R, M, $G^3$ and $G^4$ are as defined above, if appropriate in the presence of a catalyst, if appropriate in the presence of a condensing agent, if appropriate in the presence of an acid binder and if appropriate in the presence of a diluent.

The carboxylic acid derivatives of the formula (II) required as starting materials for carrying out the process (k) according to the invention have already been described in connection with the process (a) according to the invention.

The formula (XV) provides a general definition of the anilineboronic acid derivatives furthermore required as starting materials for carrying out the process (k) according to the invention. In this formula (XV), R and M preferably, particularly preferably and very particularly preferably have those meanings which have already been mentioned in connection with the description of the compounds of the formula (I) according to the invention as being preferred, particularly preferred and very particularly preferred, respectively, for these radicals. $G^3$ and $G^4$ each represent hydrogen or together represent tetramethylethylene.

The anilineboronic acid derivatives of the formula (XV) are known chemicals for synthesis or can be obtained by known processes.

It is also possible to prepare, initially, anilineboronic acid derivatives of the formula (XV-a)

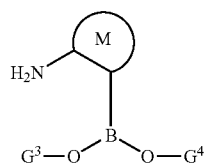

(XV-a)

in which M, $G^3$ and $G^4$ are as defined above, and then to react these, if appropriate, with halides of the formula (XIII)

$R^a$—$X^6$ (XIII)

in which $R^a$ and $X^6$ are as defined above, in the presence of a base and in the presence of a diluent. [The reaction conditions of the process (i) according to the invention apply correspondingly.]

The formula (VII) provides a general definition of the phenyl derivatives furthermore required as starting materials for carrying out the process (c) according to the invention. In this formula (VII), $Z^1$ preferably, particularly preferably and very particularly preferably has those meanings which have already been mentioned in connection with the description of the compounds of the formula (I) according to the invention as being preferred, particularly preferred and very particularly preferred, respectively, for $Z^1$. $X^3$ represents chlorine, bromine, iodine or trifluoromethylsulphonate.

The phenyl derivatives of the formula (VII) are known chemicals for synthesis.

Process d)

Using N-(2-bromophenyl)-2-iodothiophene-3-carboxamide and 4-bromo-1,2-dichlorobenzene as starting materials and also a catalyst and 4,4,4',4',5,5,5',5'-octamethyl-2,2'-bis-1,3,2-dioxaborolane, the course of the process (d) according to the invention can be illustrated by the formula scheme below.

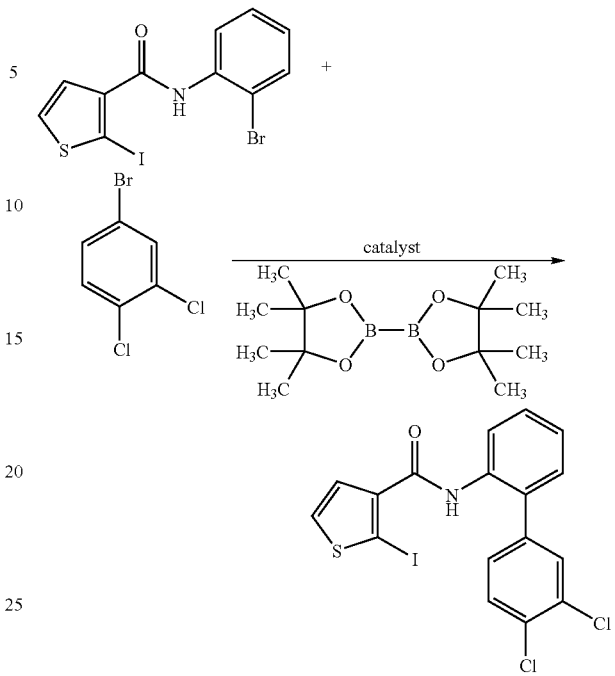

The halocarboxamides of the formula (IV) required as starting materials for carrying out the process (d) according to the invention, and the phenyl derivatives of the formula (VII), have already been described in connection with the processes (b) and (c) according to the invention.

The 4,4,4',4',5,5,5',5'-octamethyl-2,2'-bis-1,3,2-dioxaborolane furthermore required for carrying out the process (d) according to the invention is a commercially available chemical for synthesis.

Process e)

Hydrogenating, for example, N-[2-(1,3-dimethylbut-1-en-1-yl)phenyl]-2-iodothiophene-3-carboxamide, the course of the process (e) according to the invention can be illustrated by the formula scheme below.

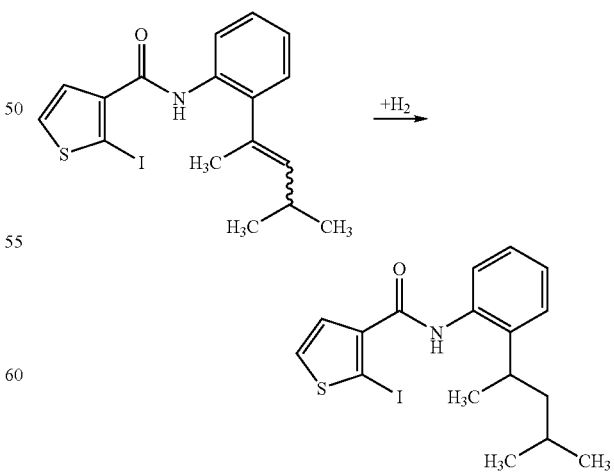

The formula (I-a) provides a general definition of the 2-halofuryl/thienyl-3-carboxamides required as starting materials for carrying out the process (e) according to the invention. In this formula (I-a) A, Hal, R and M preferably, particularly preferably and very particularly preferably have those meanings which have already been mentioned in connection with the description of the compounds of the formula (I) according to the invention as being preferred, particularly preferred and very particularly preferred, respectively, for these radicals.

$X^4$ preferably represents $C_2$-$C_{20}$-alkenyl or $C_2$-$C_{20}$-alkynyl, each of which is optionally mono- or polysubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and $C_1$-$C_4$-haloalkyl.

$X^4$ particularly preferably represents $C_2$-$C_{20}$-alkenyl or $C_2$-$C_{20}$-alkynyl, each of which is optionally substituted by fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^8R^9R^{10}$, cyclopropyl, dichlorocyclopropyl, cyclobutyl, cyclopentyl or cyclohexyl.

$X^4$ very particularly preferably represents $C_2$-$C_{20}$-alkenyl or $C_2$-$C_{20}$-alkynyl.

The compounds of the formula (I-a) are compounds according to the invention and can be prepared by process (a), (f), (g) or (h) according to the invention.

Process (f)

Dehydrating, for example, N-[2-(1-hydroxy-1,3-dimethylbutyl)phenyl]-2-iodothiophene-3-carboxamide, the course of the process (f) according to the invention can be illustrated by the formula scheme below.

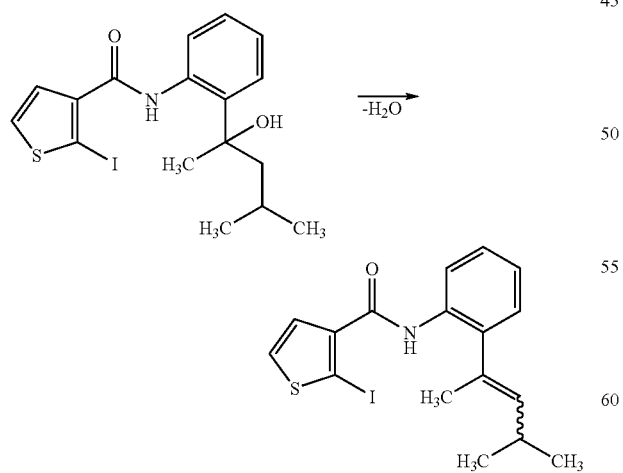

The formula (VIII) provides a general definition of the hydroxyalkylcarboxamides required as starting materials for carrying out the process (f) according to the invention. In this formula (VIII), A, Hal, R and M preferably, particularly preferably and very particularly preferably have those meanings which have already been mentioned in connection with the description of the compounds of the formula (I) according to the invention as being preferred, particularly preferred and very particularly preferred, respectively, for these radicals.

$X^5$ preferably represents $C_2$-$C_{12}$-hydroxyalkyl which is optionally additionally mono- to tetrasubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-Cycloalkyl, where the cycloalkyl moiety for its part may optionally be substituted by halogen and/or $C_1$-$C_4$-alkyl.

$X^5$ particularly preferably represents in each case straight-chain or branched hydroxyethyl, hydroxypropyl, hydroxybutyl, hydroxypentyl, hydroxyhexyl, hydroxyheptyl, hydroxyoctyl, hydroxynonyl or hydroxydecyl, each of which may be attached at any position and is optionally mono- to tetrasubstituted by identical or different substituents from the group consisting of fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^8R^9R^{10}$, cyclopropyl, dichlorocyclopropyl, cyclobutyl, cyclopentyl and cyclohexyl.

The compounds of the formula (VIII) have hitherto not been disclosed and, as novel compounds, also form part of the subject-matter of the present application.

It has also been found that the hydroxyalkylpyrazolylcarboxamides of the formula (VIII) have very good microbicidal properties and can be used both in crop protection and in the protection of materials for controlling unwanted microorganisms.

The hydroxyalkylpyrazolylcarboxamides of the formula (VIII) are obtained when l) carboxylic acid derivatives of the formula (II)

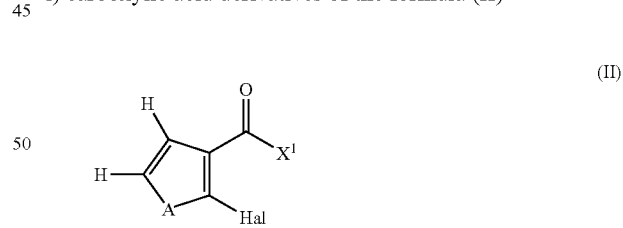

in which A, Hal and $X^1$ are as defined above
are reacted with hydroxyalkylaniline derivatives of the formula (XVI)

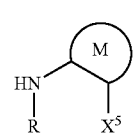

in which R, M and $X^5$ are as defined above, if appropriate in the presence of a catalyst, if appropriate in the presence of a condensing agent, if appropriate in the presence of an acid binder and if appropriate in the presence of a diluent.

The carboxylic acid derivatives of the formula (II) required as starting materials for carrying out the process (l) according to the invention have already been described in connection with the process (a) according to the invention.

The formula (XVI) provides a general definition of the hydroxyalkylaniline derivatives furthermore required as starting materials for carrying out the process (l) according to the invention. In this formula (XVI), R, M and $X^5$ preferably, particularly preferably and very particularly preferably have those meanings which have already been mentioned in connection with the description of the compounds of the formulae (I) and (VIII) according to the invention as being preferred, particularly preferred and very particularly preferred, respectively, for these radicals.

The hydroxyalkylaniline derivatives of the formula (XVI) are known and/or can be obtained by known methods (cf., for example, U.S. Pat. No. 3,917,592 or EP-A 0 824 099).

It is also possible to prepare, initially, hydroxyalkylaniline derivatives of the formula (XVI-a)

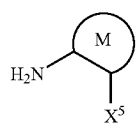

(XVI-a)

in which M, and $X^5$ are as defined above and then to react these, if appropriate, with halides of the formula (XIII)

$$R^a\text{—}X^6 \quad (XIII)$$

in which $R^a$ and $X^6$ are as defined above, in the presence of a base and in the presence of a diluent. [The reaction conditions of the process (i) according to the invention apply correspondingly.]

Process (g)

Using, for example, N-(2-bromophenyl)-2-iodothiophene-3-carboxamide and 3-methylbut-1-yne as starting materials and a catalyst, the course of the process (g) according to the invention can be illustrated by the formula scheme below.

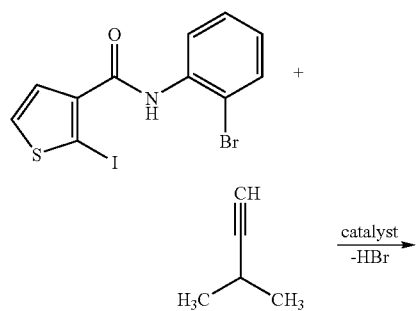

-continued

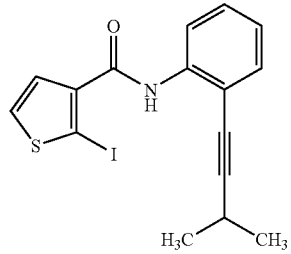

The halocarboxamides of the formula (IV) required as starting materials for carrying out the process (g) according to the invention have already been described in connection with the process (c) according to the invention.

The formula (IX) provides a general definition of the alkynes furthermore required as starting materials for carrying out the process (g) according to the invention.

$G^5$ preferably represents $C_2$-$C_{10}$-alkyl which is optionally mono- to tetrasubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-cycloalkyl, where the cycloalkyl moiety for its part may optionally be substituted by halogen and/or $C_1$-$C_4$-alkyl.

$G^5$ particularly preferably represents in each case straight-chain or branched ethyl, propyl, butyl, pentyl, hexyl, heptyl or octyl, each of which may be attached in any position and is optionally mono- to tetrasubstituted by identical or different substituents from the group consisting of fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^8R^9R^{10}$, cyclopropyl, difluorocyclopropyl, cyclobutyl, cyclopentyl and cyclohexyl.

The alkynes of the formula (IX) are known chemicals for synthesis.

The formula (X) provides a general definition of the alkenes furthermore, alternatively, required as starting materials for carrying out the process (g) according to the invention.

$G^6$, $G^7$ and $G^8$ independently of one another preferably each represent hydrogen or alkyl which is optionally mono- to tetrasubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl) amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-cycloalkyl, where the cycloalkyl moiety for its part may optionally be substituted by halogen and/or $C_1$-$C_4$-alkyl and the total number of carbon atoms of the open-chain molecular moiety does not exceed the number 12.

$G^6$, $G^7$ and $G^8$ independently of one another particularly preferably each represent hydrogen or in each case straight-chain or branched ethyl, propyl, butyl, pentyl, hexyl, heptyl or octyl, each of which may be attached in any position and is optionally mono- to tetrasubstituted by identical or different substituents from the group consisting of fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^8R^9R^{10}$, cyclopropyl, difluorocyclopropyl, cyclobutyl, cyclopentyl and cyclohexyl, where the total number of carbon atoms of the open-chain molecular moiety does not exceed the number 12.

The alkenes of the formula (X) are known chemicals for synthesis.

Process (h)

Using N-(2-acetylphenyl)-2-iodothiophene-3-carboxamide and triphenyl(propyl)phosphonium iodide as starting materials, the course of the process (h) according to the invention can be illustrated by the formula scheme below:

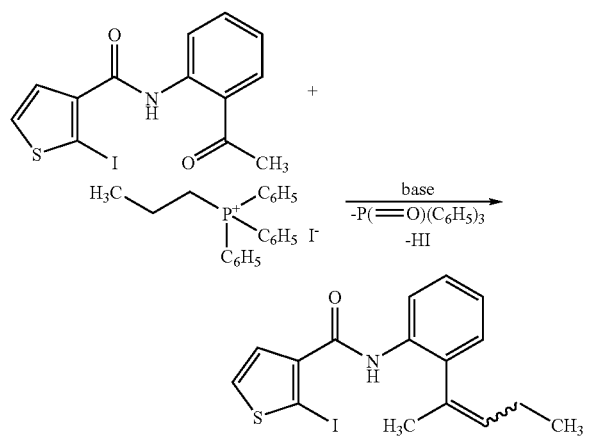

The formula (XI) provides a general definition of the ketones required as starting materials for carrying out the process (h) according to the invention. In this formula, A, Hal, R and M preferably, particularly preferably and very particularly preferably have those meanings which have already been mentioned in connection with the description of the compounds of the formula (I) according to the invention as being preferred, particularly preferred and very particularly preferred, respectively, for these radicals.

$G^9$ preferably represents $C_2$-$C_{10}$-alkyl which is optionally mono- to tetrasubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-cycloalkyl, where the cycloalkyl moiety for its part may optionally be substituted by halogen and/or $C_1$-$C_4$-alkyl.

$G^9$ particularly preferably represents in each case straight-chain or branched ethyl, propyl, butyl, pentyl, hexyl, heptyl or octyl, each of which may be attached in any position and is optionally mono- to tetrasubstituted by identical or different substituents from the group consisting of fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^8R^9R^{10}$, cyclopropyl, difluorocyclopropyl, cyclobutyl, cyclopentyl and cyclohexyl.

The ketones of the formula (XI) have hitherto not been disclosed. As novel chemical compounds, they also form part of the subject-matter of the present application. They are obtained when m) carboxylic acid derivatives of the formula (II)

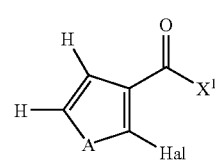

in which A, Hal and $X^1$ are as defined above
are reacted with ketoanilines of the formula (XVII)

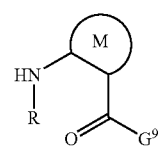

in which

R, M and $G^9$ are as defined above, if appropriate in the presence of a catalyst, if appropriate in the presence of a condensing agent, if appropriate in the presence of an acid binder and if appropriate in the presence of a diluent.

The carboxylic acid derivatives of the formula (II) required as starting materials for carrying out the process (m) according to the invention have already been described in connection with the process (a) according to the invention.

The formula (XVII) provides a general definition of the ketoanilines furthermore required as starting materials for carrying out the process (m) according to the invention. In this formula (XVII), R, M and $G^9$ preferably, particularly preferably and very particularly preferably have those meanings which have already been mentioned in connection with the description of the compounds of the formulae (I) and (XI) according to the invention as being preferred, particularly preferred and very particularly preferred, respectively, for these radicals.

The ketoanilines of the formula (XVII) are generally customary chemicals for synthesis (cf., for example, J. Am. Chem. Soc. 1978, 100, 4842-4857 or U.S. Pat. No. 4,032, 573).

It is also possible to prepare, initially, hydroxyalkylaniline derivatives of the formula (XVII-a)

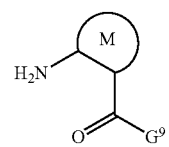

in which M and $G^9$ are as defined above and then to react these, if appropriate, with halides of the formula (XIII)

$$R^a-X^6 \quad (XIII)$$

in which $R^a$ and $X^6$ are as defined above, in the presence of a base and in the presence of a diluent.

[The reaction conditions of the process (i) according to the invention apply correspondingly.]

The formula (XII) provides a general definition of the phosphorus compounds furthermore required as starting materials for carrying out the process (h) according to the invention.

$G^{10}$ preferably represents $C_2$-$C_{10}$-alkyl which is optionally mono- to tetrasubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-C-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-cycloalkyl, where the cycloalkyl moiety for its part may optionally be substituted by halogen and/or $C_1$-$C_4$-alkyl.

$G^{10}$ particularly preferably represents in each case straight-chain or branched ethyl, propyl, butyl, pentyl, hexyl, heptyl or octyl, each of which may be attached in any position and is optionally mono- to tetrasubstituted by identical or different substituents from the group consisting of fluorine, chlorine, bromine, iodine, $C_1$-$C_6$-alkylthio, $C_1$-$C_4$-alkylsulphinyl, $C_1$-$C_4$-alkylsulphonyl, $C_1$-$C_4$-alkoxy, $C_1$-$C_4$-alkylamino, di($C_1$-$C_4$-alkyl)amino, $C_1$-$C_4$-haloalkylthio, $C_1$-$C_4$-haloalkylsulphinyl, $C_1$-$C_4$-haloalkylsulphonyl, $C_1$-$C_4$-haloalkoxy, $C_1$-$C_4$-haloalkylamino, halo-di($C_1$-$C_4$-alkyl)amino having in each case 1 to 9 fluorine, chlorine and/or bromine atoms, —$SiR^8R^9R^{10}$, cyclopropyl, difluorocyclopropyl, cyclobutyl, cyclopentyl and cyclohexyl.

Px preferably represents a grouping —$P^+(C_6H_5)_3$ $Cl^-$, —$P^+(C_6H_5)_3$ $Br^-$, —$P^+(C_6H_5)_3$ $I^-$, —$P(=O)(OCH_3)_3$ or —$P(=O)(OC_2H_5)_3$.

The phosphorus compounds of the formula (XII) are known and/or can be prepared by known processes (cf., for example, Justus Liebigs Ann. Chem. 1953, 580, 44-57 or Pure Appl. Chem. 1964, 9, 307-335).

Process (i)

Using N-[2-(1,3-dimethylbutyl)phenyl]-2-iodothiophene-3-carboxamide and acetyl chloride as starting materials, the course of the process (i) according to the invention can be illustrated by the formula scheme below:

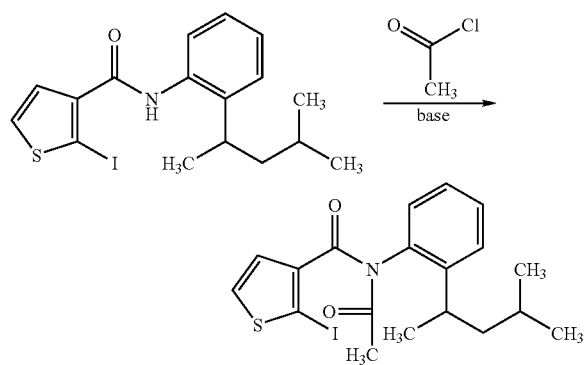

The formula (I-b) provides a general definition of the 2-halofuryl/thienyl-3-carboxamides required as starting materials for carrying out the process (i) according to the invention. In this formula (I-b), A, Hal, M and Z preferably, particularly preferably and very particularly preferably have those meanings which have already been mentioned in connection with the description of the compounds of the formula (I) according to the invention as being preferred, particularly preferred and very particularly preferred, respectively, for these radicals.

The compounds of the formula (I-b) are compounds according to the invention and can be prepared by processes (a) to (h).

The formula (XIII) provides a general definition of the halides furthermore required as starting materials for carrying out the process (i) according to the invention. In this formula (XIII), $R^a$ preferably, particularly preferably and very particularly preferably has those meanings which have already been mentioned above, for the compounds of the formula (I-c), as being preferred, particularly preferred and very particularly preferred, respectively, for this radical. $X^6$ represents chlorine, bromine or iodine.

Halides of the formula (XIII) are known.

Reaction Conditions

Suitable diluents for carrying out the processes (a), (j), (k), (l) and (m) according to the invention are all inert inorganic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water.

The processes (a), (j), (k), (l) and (m) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, lithium diisopropylamide, sodium methoxide, sodium ethoxide, potassium tert-butoxide, sodium hydroxide potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The processes (a), (j), (k), (l) and (m) according to the invention are, if appropriate, carried out in the presence of a suitable condensing agent. Suitable condensing agents are all condensing agents which can customarily be used for such amidation reactions. Examples which may be mentioned are acid halide formers, such as phosgene, phosphorus tribromide, phosphorus trichloride, phosphorus pentachloride, phosphorus oxychloride or thionylchloride; anhydride formers, such as ethyl chloroformate, methyl chloroformate, isopropyl chloroformate, isobutyl chloroformate or methane sulphonyl chloride; carbodiimides, such as N,N'-dicyclohexylcarbodiimide (DCC), or other customary condensing agents, such as phosphorus pentoxide, polyphosphoric acid, N,N'-carbonyldiimidazole, 2-ethoxy-N-ethoxycarbonyl-1,2-dihydroquinoline (EEDQ), triphenylphosphine/carbon tetrachloride or bromotripyrrolidinophosphonium hexafluorophosphate.

The processes (a), (j), (k), (l) and (m) according to the invention are, if appropriate, carried out in the presence of a catalyst. Examples which may be mentioned are 4-dimethylaminopyridine, 1-hydroxybenzotriazole or dimethylformamide.

When carrying out the processes (a), (j), (k), (l) and (m) according to the invention, the reaction temperatures may be varied within a relatively wide range. In general, the processes are carried out at temperatures of from 0° C. to 150° C., preferably at temperatures of from 0° C. to 80° C.

For carrying out the process (a) according to the invention for preparing the compounds of the formula (I), in general from 0.8 to 15 mol, preferably from 0.8 to 8 mol, of aniline derivative of the formula (III) are employed per mole of the carboxylic acid derivative of the formula (II).

For carrying out the process (j) according to the invention for preparing the compounds of the formula (IV), in general from 0.8 to 15 mol, preferably from 0.8 to 8 mol, of haloaniline of the formula (XIV) are employed per mole of the carboxylic acid derivative of the formula (II).

For carrying out the process (k) according to the invention for preparing the compounds of the formula (VI), in general from 0.8 to 15 mol, preferably from 0.8 to 8 mol, of aniline boronic acid derivative of the formula (XV) are employed per mole of the carboxylic acid derivative of the formula (II).

For carrying out the process (l) according to the invention for preparing the compounds of the formula (VIII), in general from 0.8 to 15 mol, preferably from 0.8 to 8 mol, of hydroxyalkylaniline derivative of the formula (XVI) are employed per mole of the carboxylic acid derivative of the formula (II).

For carrying out the process (m) according to the invention for preparing the compounds of the formula (IX), in general from 0.8 to 15 mol, preferably from 0.8 to 8 mol, of ketoaniline of the formula (XVII) are employed per mole of the carboxylic acid derivative of the formula (II).

Suitable diluents for carrying out the processes (b), (c) and (d) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

When carrying out the processes (b), (c) and (d) according to the invention, the reaction temperatures can be varied within a relatively wide range. In general, the processes are carried out at temperatures of from 0° C. to 180° C., preferably at temperatures of from 20° C. to 150° C.

The processes (b), (c) and (d) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, fluorides, phosphates, carbonates or bicarbonates, such as, for example, sodium hydride, sodium amide lithium diisopropylamide, sodium methoxide, sodium ethoxide, potassium tert-butoxide, sodium hydroxide, potassium hydroxide, sodium acetate, sodium phosphate, potassium phosphate, potassium fluoride, caesium fluoride, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The processes (b), (c) and (d) according to the invention are carried out in the presence of a catalyst, such as, for example, a palladium salt or complex. These are preferably palladium chloride, palladium acetate, tetrakis(triphenylphosphine)palladium, bis(triphenylphosphine)palladium dichloride or 1,1'-bis(diphenylphosphino)ferrocenepalladium(II) chloride.

It is also possible to generate a palladium complex in the reaction mixture by adding a palladium salt and a complex ligand, such as, for example, triethylphosphane, tri-tert-butylphosphane, tricyclohexylphosphane, 2-(dicyclohexylphosphane)biphenyl, 2-(di-tert-butylphosphane)biphenyl, 2-(dicyclohexylphosphane)-2'-(N,N-dimethylamino)biphenyl, triphenylphosphane, tris-(o-tolyl)phosphane, sodium 3-(diphenylphosphino)benzenesulphonate, tris-2-(methoxyphenyl)phosphane, 2,2'-bis(diphenylphosphane)-1,1'-binaphthyl, 1,4-bis(diphenylphosphane)butane, 1,2-bis(diphenylphosphane)-ethane, 1,4-bis(dicyclohexylphosphane)butane, 1,2-bis(dicyclohexylphosphane)ethane, 2-(dicyclohexylphosphane)-2'-(N,N-diethylamino)biphenyl, bis(diphenylphosphino)ferrocene or tris-(2,4-tert-butylphenyl)phosphite separately to the reaction mixture.

For carrying out the process (b) according to the invention for preparing the compounds of the formula (I), in general from 1 to 15 mol, preferably from 2 to 8 mol, of boronic acid derivative of the formula (V) are added per mole of the halocarboxamide of the formula (IV).

For carrying out the process (c) for preparing the compounds of the formula (I), in general from 0.8 to 15 mol, preferably from 0.8 to 8 mol, of phenyl derivative of the formula (VII) are employed per mole of the boronic acid derivative of the formula (VI).

For carrying out the process (d) according to the invention for preparing the compounds of the formula (I), in general from 0.8 to 15 mol, preferably from 0.8 to 8 mol, of phenyl derivative of the formula (VII) and from 0.8 to 15 mol, preferably from 0.8 to 8 mol, of 4,4,4',4',5,5,5',5'-octamethyl-2,2'-bis-1,3,2-dioxaborolane are employed per mole of the halocarboxamide of the formula (IV).

Suitable diluents for carrying out the process (e) according to the invention are all inert organic solvents. These preferably include aliphatic or alicyclic hydrocarbons, such as, for example, petroleum ether, hexane, heptane, cyclohexane, methylcyclohexane or decalin; ethers, such as diethyl ether, diisopropyl ether, methyl t-butyl ether, methyl tert-amyl ether, dioxane, tetrahydrofuran, 1,2-dimethoxyethane or 1,2-diethoxyethane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

The process (e) according to the invention is carried out in the presence of a catalyst. Suitable catalysts are all catalysts customarily used for hydrogenations. Examples which may be mentioned are: Raney-nickel, palladium or platinum, if appropriate on a support, such as, for example, activated carbon.

When carrying out the process (e) according to the invention, the reaction temperatures can be varied within a relatively wide range. In general, the process is carried out at temperatures of from 0° C. to 150° C., preferably at temperatures of from 20° C. to 100° C.

Suitable diluents for carrying out the process (f) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethylsulphoxide; sulphones, such as sulpholane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

The process (f) according to the invention is, if appropriate, carried out in the presence of an acid. Suitable acids are all inorganic and organic protic and Lewis acids, and also all polymeric acids. These include, for example, hydrogen chloride, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, titanium tetrachloride, tetrabutyl orthotitanate, zinc chloride, iron(III) chloride, antimony pentachloride, acid ion exchangers, acid aluminas and acid silica gel.

When carrying out the process (f) according to the invention, the reaction temperatures can be varied within a relatively wide range. In general, the process is carried out at temperatures of from 0° C. to 150° C., preferably at temperatures of from 0° C. to 100° C.

Suitable diluents for carrying out the process (g) according to the invention are all inert organic solvents. These preferably include nitriles, such as acetonitrile, propionitrile, n- or i-butyronitrile or benzonitrile or amides, such as N,N-dimethylformanide, N,N-dimethylacetamide, N-methylformanilide, N-methylpyrrolidone or hexamethylphosphoric triamide.

The process (g) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (g) according to the invention is carried out in the presence of one or more catalysts.

Suitable for this purpose are in particular palladium salts or palladium complexes. These are preferably palladium chloride, palladium acetate, tetrakis(triphenylphosphine)palladium or bis(triphenylphosphine)palladium dichloride. It is also possible to generate a palladium complex in the reaction mixture by adding a palladium salt and a complex ligand separately to the reaction mixture.

Suitable ligands are preferably organophosphorus compounds. Examples which may be mentioned are: triphenylphosphine, tri-o-tolylphosphine, 2,2'-bis(diphenylphosphino)-1,1'-binaphthyl, dicyclohexylphosphinebiphenyl, 1,4-bis(diphenylphosphino)butane, bisdiphenylphosphinoferrocene, di-(tert-butylphosphino)biphenyl, di(cyclohexylphosphino)biphenyl, 2-dicyclohexylphosphino-2'-N,N-dimethylaminobiphenyl, tricyclohexylphosphine, tri-tert-butylphosphine. However, ligands may also be dispensed with.

The process (g) according to the invention is furthermore, if appropriate, carried out in the presence of a further metal salt such as a copper salt, for example copper(I) iodide.

When carrying out the process (g) according to the invention, the reaction temperatures can be varied within a relatively wide range. In general, the process is carried out at temperatures of from 20° C. to 180° C., preferably a temperatures of from 50° C. to 150° C.

For carrying out the process (g) according to the invention for preparing the compounds of the formula (I), in general from 1 to 5 mol, preferably from 1 to 2 mol, of an alkyne of the formula (IX) or an alkene of the formula (X) are employed per mole of the halocarboxamide of the formula (IV).

Suitable diluents for carrying out the process (h) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl tert-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether.

The process (h) according to the invention is, if appropriate, carried out in the presence of a suitable acid acceptor. Suitable acid acceptors are all customary strong bases. These preferably include alkaline earth metal or alkali metal hydrides, hydroxides, amides, alkoxides or alkali metal hydrocarbon compounds, such as, for example, sodium hydride, sodium hydroxide, potassium hydroxide, sodium amide, lithium diisopropylamide, sodium methoxide, sodium ethoxide, potassium tert-butoxide, methyllithium, phenyllithium or butyllithium.

When carrying out the process (h) according to the invention, the reaction temperatures can be varied within a relatively wide range. In general, the process is carried out at temperatures of from −80° C. to 150° C., preferably at temperatures of from −30° C. to 80° C.

For carrying out the process (h) according to the invention for preparing the compounds of the formula (I), in general from 1 to 5 mol, preferably from 1 to 2 mol, of phosphorus compound of the formula (XII) are employed per mole of the ketone of the formula (XI).

Suitable diluents for carrying out the process (i) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; or amides, such as N,N-dimethylformamide, N,N-dimethylacetamide, N-methylformanilide, N-methylpyrrolidone or hexamethylphosphoric triamide.

The process (i) according to the invention is carried out in the presence of a base. Suitable bases are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (i) according to the invention, the reaction temperatures can be varied within a relatively wide range. In general, the process is carried out at temperatures of from 0° C. to 150° C., preferably at temperatures of from 20° C. to 110° C.

For carrying out the process (i) according to the invention for preparing the compounds of the formula (I), in general from 0.2 to 5 mol, preferably from 0.5 to 2 mol, of halide of the formula (XIII) are employed per mole of the 2-halofuryl/thienyl-3-carboxamide of the formula (I-b).

Reaction Conditions for Processes (1) to (4) from Scheme 1:

Suitable diluents for carrying out process (1) in scheme 1 are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; or amides, such as N,N-dimethylformamide, N,N-dimethylacetamide, N-methylformanilide, N-methylpyrrolidone or hexamethylphosphoric triamide; alcohols, such as methanol, ethanol, isopropanol.

Process (1) in scheme 1 is carried out in the presence of a suitable reducing agent. Suitable reducing agents are all customary inorganic or organic reducing agents. These preferably include alkaline earth metal or alkali metal hydrides, such as, for example, sodium hydride, or complex hydrides, such as, for example, lithium aluminium hydride, sodium borohydride, sodium cyanoborohyolride, diisobutylaluminium hydride, borane, diborane or borane complexes, such as, for example, borane-pyridine, silanes, such as, for example, triethylsilane, metals, such as, for example, sodium, lithium, zinc, iron, or hydrogen.

Process (1) in scheme 1 is, if appropriate, carried out in the presence of a suitable acid or Lewis acid. Suitable acids/Lewis acids are all acids/Lewis acids which may customarily be used for such acid/Lewis-acid-mediated reductions. Examples which may be mentioned are hydrochloric acid, acetic acid, trifluoroacetic acid, boron trifluoride or complex boron trifluorides, such as, for example, boron trifluoride etherate, aluminium trichloride, cerium trichloride, inorganic or organic titanium compounds, such as, for example, titanium tetrachloride, titanium tetraisopropoxide.

Process (1) in scheme 1 is, if appropriate, carried out in the presence of a catalyst. Examples which may be mentioned are metals or metal salts, in particular transition metals or salts thereof, such as, for example, platinum, palladium, nickel (Raney-nickel), iridium, rhodium, osmium, iron, ruthenium, cobalt. These metals or metal salts can, if appropriate, also be bound or applied to resins or surfaces or supports (for example carbons).

When carrying out process (1) in scheme 1, the reaction temperatures can be varied within a relatively wide range. In general, the process is carried out at temperatures of from 0° C. to 200° C., preferably a temperatures of from 0° C. to 150° C.

When the reducing agent used in process (1) in scheme 1 is hydrogen, the pressure can be varied within a relatively wide range. In general, the process is carried out at pressures of from 1 bar to 300 bar, preferably from 1 bar to 100 bar.

For carrying out process (1) in scheme 1, in general from 0.2 to 10 mol, preferably from 0.5 to 5 mol, of reducing agent are employed per mole of starting material.

Suitable diluents for carrying out process (2) in scheme 1 are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; or amides, such as N,N-dimethylformamide, N,N-dimethylacetamide, N-methylformanilide, N-methylpyrrolidone or hexamethylphosphoric triamide.

Process (2) in schema 1 is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Process (2) in scheme 1 is carried out in the presence of a suitable halogenating agent. Suitable halogenating agents are all halogenating agents which may customarily be used for such halogenation reactions. Examples which may be mentioned are halide formers, such as phosgene, phosphorus tribromide, phosphorus trichloride, phosphorus pentachloride, phosphorus oxychloride, oxalyl chloride or thionyl chloride; anhydride formers, such as ethyl chloroformate, methyl chloroformate, isopropyl chloroformate, isobutyl chloroformate or methanesulphonyl chloride; or other customary condensing agents, such as phorphorus pentoxide, polyphosphoric acid, N,N'-carbonyldiimidazole, 2-ethoxy-N-ethoxycarbonyl-1,2-dihydroquinoline (EEDQ), triphenylphosphine/carbon tetrachloride or bromotripyrrolidinophosphonium hexafluorophosphate.

Process (2) in scheme 1 is, if appropriate, carried out in the presence of a catalyst. Examples which may be mentioned are 4-dimethylaminopyridine, 1-hydroxybenzotriazole or dimethylformamide.

When carrying out process (2) in scheme 1, the reaction temperatures may be varied within a relatively wide range. In general, the process is carried out at temperatures of from 0° C. to 200° C., preferably at temperatures of from 0° C. to 150° C.

For carrying out process (2) in scheme 1, in general from 0.2 to 10 mol, preferably from 0.5 to 5 mol, of halogenating agent are employed per mole of starting material.

Suitable diluents for carrying out process (3) in scheme 1 are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; or amides, such as N,N-dimethylformamide, N,N-dimethylacetamide, N-methylformanilide N-methylpyrrolidone or hexamethylphosphoric triamide.

Process (3) in schema 1 is carried out in the presence of a base. Suitable bases are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out process (3) in scheme 1, the reaction temperatures can be varied within a relatively wide range. In general, the process is carried out at temperatures of from 0° C. to 200° C., preferably at temperatures of from 20° C. to 150° C.

For carrying out process (3) in scheme 1, in general from 0.2 to 5 mol, preferably from 0.5 to 2 mol, of a compound of the formula H—$Z^{3-C}$ are employed per mole of starting material.

Suitable diluents for carrying out process (4) in scheme 1 are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl tert-amyl ether, dioxane, tetrahydrofuran, 1,2-dimethoxyethane, 1,2-diethoxyethane or anisole; amides, such as N,N-dimethylformamide, N,N-dimethylacetamide, N-methylformanilide, N-methylpyrrolidone or hexamethylphosphoric triamide; sulphoxides, such as dimethyl sulphoxide; sulphones, such as sulpholane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, triethylene glycol, mixtures thereof with water or pure water.

Process (4) in scheme 1 is carried out in the presence of a metal. Suitable metals are, preferably, transition metals, such as for example, palladium platinum, rhodium, nickel (Raney-nickel), iron, cobalt, ruthenium, iridium, zinc or osmium. The metals may, if appropriate, be attached to supports, such as, for example, carbon, resins, zeolites, alkali metal or alkaline earth metal sulphates.

Process (4) in scheme 1 is carried out in the presence of a reducing agent. Suitable reducing agents are, preferably, elemental hydrogen, formate salts, preferably alkali metal formate salts, such as, for example, sodium formate, but also ammonium formate, or else metal hydrides or complex metal hydrides, such as, for example, lithium aluminium hydride, sodium borohydride.

Process (4) in scheme 1 can be carried out in the presence of acids. Suitable acids are, preferably, organic acids, such as, for example, formic acid, acetic acid, ascorbic acid, but also mineral acids, such as, for example, hydrochloric acid or sulphuric acid.

Process (4) in scheme 1 can be carried out in the presence of bases. Suitable bases are, preferably, organic bases, such as, for example, pyridine, but also aqueous solutions of alkali metal or alkaline earth metal hydroxides, such as, for example, sodium hydroxide or barium hydroxide.

When carrying out process (4) in scheme 1, the reaction temperatures can be varied within a relatively wide range. In general, the process is carried out at temperatures of from −80° C. to 300° C., preferably at temperatures of from 0° C. to 200° C.

If elemental hydrogen is used, process (4) in scheme 1 is carried out under a hydrogen pressure between 0.5 and 200 bar, preferably between 1 and 100 bar.

For carrying out process (4) in scheme 1, in general from 0.8 to 1000 mol, preferably from 1 to 500 mol, of reducing agent (ammonium formate, hydride etc.) are employed per mole of starting material.

Reaction Conditions for Processes (5) to (11) from Scheme 2:

Suitable diluents for carrying out process (5) are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl tert-amyl ether, dioxane, tetrahydrofuran, 1,2-methoxyethane, 1,2-diethoxyethane or anisole.

Process (5) is carried out in the presence of an organometallic compound. Suitable organometallic compounds are, preferably, organolithium compounds, such as n-, sec-, or tert-butyllithium, phenyllithium or methyllithium.

When carrying out process (5), the reaction temperatures can be varied within a relatively wide range. In general, the process is carried out at temperatures of from 120° C. to 100° C., preferably at temperatures of from 80° C. to 20° C.

For carrying out process (5), in general from 0.2 to 5 mol, preferably from 0.5 to 2 mol, of ester of the formula $Z^{3-E}$—$CO_2R^{17}$ are employed per mole of starting material.

Suitable diluents for carrying out process (6) are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; sulphoxides, such as dimethyl sulphoxide; sulphones, such as sulpholane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, triethylene glycol, mixtures thereof with water or pure water.

Process (6) is carried out in the presence of an acid. Suitable acids are, preferably, mineral acids, such as, for example, hydrochloric acid, hydroiodic acid or hydrobromic acid, sulphuric acid, or else organic acids, for example trifluoroacetic acid, trifluoromethanesulphonic acid.

When carrying out process (6), the reaction temperatures can be varied within a relatively wide range. In general, the process is carried out at temperatures of from 0° C. to 300° C., preferably at temperatures of from 20° C. to 200° C.

For carrying out process (6), in general from 0.1 to 10 000 mol, preferably from 1 to 2000 mol, of acid are employed per mole of starting material.

Suitable diluents for carrying out process (7) are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-diethylacetamide, N-methylformanilide, N-methylpyrrolidone or hexamethylphosphoric triamide; sulphoxides, such as dimethyl sulphoxide; sulphones, such as sulpholane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, triethylene glycol, mixtures thereof with water or pure water.

Process (7) is carried out in the presence of a base. Suitable bases are, preferably, alkaline earth metal or alkali metal hydroxides, such as, for example, sodium hydroxide, potassium hydroxide, ammonium hydroxide.

When carrying out process (7), the reaction temperatures can be varied within a relatively wide range. In general, the process is carried out at temperatures of from 100° C. to 300° C., preferably at temperatures of from 150° C. to 250° C.

For carrying out process (7), in general from 0.2 to 5 mol, preferably from 0.5 to 3 mol, of hydrazine or hydrazine hydrate are employed per mole of starting material.

Suitable diluents for carrying out process (8) are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butylether, methyl tert-amyl ether, dioxane, tetrahydrofuran, 1,2-dimethoxyethane, 1,2-diethoxyethane or anisole.

Process (8) is carried out in the presence of an organometallic compound. Suitable organometallic compounds are, preferably, methyl magnesium chloride, bromide or iodide or methyllithium.

When carrying out process (8), the reaction temperatures can be varied within a relatively wide range. In general, the process is carried out at temperatures of from 120° C. to 200° C., preferably at temperatures of from −80° C. to 100° C.

For carrying out process (8), in general from 0.8 to 10 mol, preferably from 1 to 5 mol, of organometallic compound are employed per mole of starting material.

Suitable diluents for carrying out process (9) are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

Process (9) is, if appropriate, carried out in the presence of an acid. Suitable acids are all inorganic and organic protic acids and Lewis acids, and also all polymeric acids. These include, for example, hydrogen chloride, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, titanium tetrachloride, tetrabutyl orthotitanate, zinc chloride, iron(III) chloride, antimony pentachloride, acidic ion exchangers, acidic aluminas and acidic silica gel.

When carrying out process (9), the reaction temperatures may be varied within a relatively wide range. In general, the process is carried out at temperatures of from 0° C. to 150° C., preferably at temperatures of from 0° C. to 80° C.

Processes (9) and (10) can also be carried out in a tandem reaction ("one-pot reaction").

Suitable diluents for carrying out process (10) are all inert organic solvents. These preferably include aliphatic or alicyclic hydrocarbons, such as, for example, petroleum ether, hexane, heptane, cyclohexane, methylcyclohexane or decalin; ethers, such as diethyl ether, diisopropyl ether, methyl tert-butyl ether, methyl tert-amyl ether, dioxane, tetrahydrofuran, 1,2-dimethoxyethane or 1,2-diethoxyethane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

Process (10) is carried out in the presence of a catalyst. Suitable catalysts are all catalysts which are customarily used for hydrogenations. Examples which may be mentioned are: Raney-nickel, palladium or platinum, if appropriate on a support, such as, for example, activated carbon.

Instead of in the presence of hydrogen in combination with a catalyst, the hydrogenation in process (10) can also be carried out in the presence of triethylsilane.

When carrying out process (10), the reaction temperatures can be varied within a relatively wide range. In general, the process is carried out at temperatures of from 0° C. to 150° C., preferably at temperatures of from 20° C. to 100° C.

Process (10) is carried out under a hydrogen pressure between 0.5 and 200 bar, preferably between 2 and 50 bar, particularly preferably between 3 and 10 bar.

Suitable diluents for carrying out process (11) are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl tert-amyl ether, dioxane, tetrahydrofuran, 1,2-dimethoxyethane, 1,2-dimethoxyethane or anisole; amides, such as N,N-dimethylformamide, N,N-dimethylacetamide, N-methylformanilide, N-methylpyrrolidone or hexamethylphosphoric triamide; sulphoxides, such as dimethyl sulphoxide; sulphones, such as sulpholane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, triethylene glycol, mixtures thereof with water or pure water.

Process (11) is carried out in the presence of a metal. Suitable metals are, preferably, transition metals, such as, for example, palladium, platinum, rhodium, nickel, iron, cobalt, ruthenium, iridium or osmium. The metals may, if appropriate, be attached to supports, such as, for example, carbon, resins, zeolites, alkali metal or alkaline earth metal sulphates.

Process (11) is carried out in the presence of a reducing agent. Suitable reducing agents are, preferably, elemental hydrogen, formate salts, preferably alkali formate salts, such as, for example, sodium formate, but also ammonium formate or else metal hydrides (hydrodehalogenation).

Process (11) can be carried out in the presence of acids. Suitable acids are, preferably, organic acids, such as, for example, formic acid, acetic acid, ascorbic acid, but also mineral acids, such as, for example, hydrochloric acid or sulphuric acid.

Process (11) can be carried out in the presence of bases. Suitable bases are, preferably, organic bases, such as, for example, pyridine, but also aqueous solutions of alkali metal or alkaline earth metal hydroxides, such as, for example, sodium hydroxide or barium hydroxide.

When carrying out process (11), the reaction temperatures can be varied within a relatively wide range. In general, the process is carried out at temperatures of from −80° C. to 300° C., preferably at temperatures of from 0° C. to 200° C.

When using elemental hydrogen, process (11) according to the invention is carried out under a hydrogen pressure between 0.5 and 200 bar, preferably between 1 and 100 bar.

For carrying out process (11) according to the invention, in general from 0.8 to 1000 mol, preferably from 1 to 500 mol, of reducing agent (ammonium formate, hydride etc.) are employed per mole of starting material.

All processes according to the invention are generally carried out under atmospheric pressure. However, it is also possible to operate under elevated or reduced pressure—in general between 0.1 bar and 10 bar.

The substances according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera,* syn: *Helminthosporium*);

*Cochliobolus* species, such as, for example, *Cochliobolus sativus* (conidia form: *Drechslera,* syn: *Helmninthosporium*);

*Uromyces* species, such as, for example, *Uromyces appendiculatus;*

*Puccinia* species, such as, for example, *Puccinia recondita*;

*Sclerotinia* species, such as, for example, *Sclerotinia sclerotiorum*;

*Tilletia* species, such as, for example, *Tilletia caries*;

*Ustilago* species, such as, for example, *Ustilago nuda* or *Ustilago avenae*;

*Pellicularia* species, such as, for example, *Pellicularia sasakii*;

*Pyricularia* species, such as, for example, *Pyricularia oryzae*;

*Fusarium* species, such as, for example, *Fusarium culmorum*;

*Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*;

*Rhizoctonia* species, such as, for example, *Rhizoctonia solani*.

The active compounds according to the invention also show a strong invigorating action in plants. Accordingly, they are suitable for mobilizing the internal defences of the plant against attack by unwanted microorganisms.

In the present context, plant-invigorating (resistance-inducing) compounds are to be understood as meaning substances which are capable of stimulating the defence system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be used with particularly good results for controlling cereal diseases, such as, for example, against *Puccinia* species, and diseases in viticulture and in the cultivation of fruit and vegetables, such as, for example, against *Botrytis, Venturia* or *Alternaria* species.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as immediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, pumice, marble, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:
2-phenylphenol; 8-hydroxyquinolin sulphate; acibenzolar-S-methyl; aldimorph; amidoflumet; ampropylfos; ampropylfos-potassium; andoprim; anilazine; azaconazole; azoxystrobin; benalaxyl; benalaxyl M; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procyrnidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrin; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; tritriconazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl) pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulphate; cufraneb; copper oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholinesterase (AChE) Inhibitors 1.1 carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulphan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)

1.2 organophosphates (for example acephate, azamethiphos, azinphos (-methyl, -ethyl), bromophosethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-s-methylsulphon, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenthrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemetonmethyl, parathion (-methyl/-ethyl), phenthoate, phorate, phosalone, phosmet, phosphamidon, phosphocarb, phoxim, pirimiphos (-methyl/ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion)

2. Sodium Channel Modulators/Blockers of Voltage-Dependent Sodium Channels 2.1 pyrethroids (for example acrinathrin, allethrin (d-cis-trans, d-trans), beta-cyfluthrbin, bifenthrin, bioallethrin, bio-alletrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermetin (alpha-, beta-, theta-, zeta-), cyphenothrin, DDT, deltamethrin, empenthrin (1R-isomer), esfenvalerate, etofenprox, fenfluthrin, fenpropathrm, fenpyrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrn, resmethrin, RU 15525, silafluofen, tau-fluvalinate, tefluthrin, terallerin, tetramethrin (1R-isomer), tralomethrin, transfluthrin, ZXI 8901, pyrethrins (pyrethrum))

2.2 oxadiazines (for example indoxacarb)

3. Acetylcholine Receptor Agonists/Antagonists 3.1 chloronicotinyls/neonicotinoids (for example acetamiprid, clothianidin, dinotefuran, imidacloprid, nitenpyram, nithiazine, thiacloprid, thiamethoxam)

3.2 nicotine, bensultap, cartap

4. Acetylcholine Receptor Modulators 4.1 spinosyns (for example spinosad)

5. Antagonists of GABA-controlled Chloride Channels 5.1 cyclodiene organochlorines (for example camphechlor, chlordane, endosulphan, ganuna-HCH, HCH, heptachlor, lindane, methoxychlor)

5.2 fiproles (for example acetoprole, ethiprole, fipronil, vaniliprole)

6. Chloride Channel Activators 6.1 mectins (for example abamectin, avermectin, emamectin, emamectin-benzoate, ivermectin, milbemectin, milbemycin)

7. Juvenile Hormone Mimetics (for example diofenolan, epofenonane, fenoxycarb, hydroprene, kinoprene, methoprene, pyriproxifen, triprene)

8. Ecdyson Agonists/Disruptors 8.1 diacylhydrazines (for example chromafenozide, halofenozide, methoxyfenozide, tebufenozide)

9. Chitin Biosynthesis Inhibitors 9.1 benzoylureas (for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron)

9.2 buprofezin 9.3 cyromazine

10. Inhibitors of Oxidative Phosphorylation, ATP Disruptors 10.1 diafenthiuron 10.2 organotins (for example azocyclotin, cyhexatin, fenbutatin-oxide)

11. Decouplers of Oxidative Phosphorylation Acting by Interrupting the H-proton Gradient 11.1 pyrroles (for example chlorfenapyr)

11.2 dinitrophenols (for example binapacyrl, dinobuton, dinocap, DNOC)

12. Side-I Electron Transport Inhibitors 12.1 METIs (for example fenazaquin, fenpyroximate, pyrimidifen, pyridaben, tebufenpyrad, tolfenpyrad)

12.2 hydramethylnon 12.3 dicofol

13. Side-II Electron Transport Inhibitors 13.1 rotenone

14. Side-III Electron Transport Inhibitors 14.1 acequinocyl, fluacrypyrim

15. Microbial Disruptors of the Insect Gut Membrane

*Bacillus thuringiensis* strains

16. Inhibitors of Fat Synthesis 16.1 tetronic acids (for example spirodiclofen, spiromesifen)

16.2 tetramic acids [for example 3-(2,5-direthylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8) and carbonic acid, cis-3-(2,5-dimethylphenyl)-8-methoxy-2-oxo-1-azaspiro[4.5]dec-3-en-4-yl ethyl ester (CAS-Reg.-No.: 203313-25-1)]

17. Carboxamides (for example flonicamid)

18. Octopaminergic Agonists (for example amitraz)

19. Inhibitors of Magnesium-stimulated ATPase (for example propargite)

20. Phthalamides (for example $N^2$-[1,1-dimethyl-2-(methylsulphonyl) ethyl]-3-iodo-$N^1$-[2-methyl-4-[1,2,2,2-tetrafluoro-1-(trifluoromethyl)ethyl]phenyl]-1,2-benzenedicarboxamide (CAS-Reg.-No.: 272451-65-7), flubendiamide)

21. Nereistoxin Analogues (for example thiocyclam hydrogen oxalate, thiosultap-sodium)

22. Biologicals, Hormones or Pheromones (for example azadirachtin, *Bacillus* spec., *Beauveria* spec., *Codlemone, Metarrhizium* spec., *Paecilomyces* spec., *Thuringiensin, Verticillium* spec.)

23. Active Compounds with Unknown or Unspecific Mechanisms of Action 23.1 fumigants (for example aluminium phosphide, methyl bromide, sulphuryl fluoride)

23.2 selective antifeedants (for example cryolite, flonicamid, pymetrozine)

23.3 mite growth inhibitors (for example clofentezine, etoxazole, hexythiazox)

23.4 amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulphluramid, tetradifon, tetrasul, triarathene, verbutin, furthermore the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage ability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosates or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Boilgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosates, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

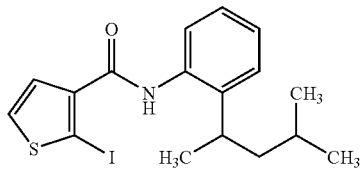

Under protective gas (argon), 0.56 ml (3.38 mmol) of N,N-diisopropylethylamine and 1.18 g (2.5 mmol) of bromotrispyrrolidinophosphonium hexafluorophosphate (PyBrop) are added to a solution of 516 mg (2.0 mmol) of 2-iodothiophene-3-carboxylic acid and 300 mg (1.7 mmol) of 2-(1,3-dimethylbutyl)phenylamine in 10 ml of acetonitrile. The reaction mixture is stirred at room temperature for 24 hours and, for work-up, added to water, extracted with ethyl acetate, dried over sodium sulphate and concentrated under reduced pressure. Column chromatography (cyclohexane/ethyl acetate gradient) gives 150 mg (21% of theory) of N-[2-(1,3-dimethylbutyl)phenyl]-2-iodothiophene-3-carboxamide [log P (pH 2.3)=4.14].

Example 2

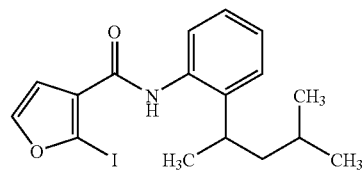

Under protective gas (argon), 0.56 ml (3.38 mmol) of N,N-diisopropylethylamine and 1.18 g (2.5 mmol) of bromotrispyrrolidinophosphonium hexafluorophosphate (PyBrop) are added to a solution of 483 mg (2.02 mmol) of 2-iodofuran-3-carboxylic acid and 300 mg (1.7 mmol) of 2-(1,3-dimethylbutyl)phenylamine in 10 ml of acetonitrile. The reaction mixture is stirred at room temperature for 24 hours and, for work-up, added to water, extracted with ethyl acetate, dried over sodium sulphate and concentrated under reduced pressure. Column chromatography (cyclohexane/ethyl acetate gradient) gives 130 mg (18% of theory) of N-[2-(1,3-dimethylbutyl)phenyl]-2-iodo-3-furamide [log P (pH 2.3)=3.88].

The compounds of the formula (I) listed in Table 1 below were also obtained analogously to Examples 1 and 2 and in accordance with the details given in the general description of the preparation processes (a) to (h) according to the invention:

TABLE 1

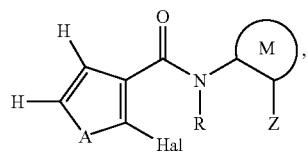

| No. | A | Hal | R | M[a] | Z[b] | logP |
|-----|---|-----|---|------|------|------|
| 3 | O | I | H | ![*,#-phenyl] | ![+-phenyl-Br] | 3.72 |

TABLE 1-continued (I)

| No. | A | Hal | R | M[a] | Z[b] | logP |
|---|---|---|---|---|---|---|
| 4 | O | I | H | phenyl (*,#) | 3-F, 4-Br-phenyl | 3.58 |
| 5 | S | I | H | phenyl (*,#) | CH₂=C-CH(CH₃)CH₃ (2-methyl-3-methylbut-1-enyl) | 4.57 |
| 6 | S | I | H | phenyl (*,#) | CH(CH₃)CH₂C(CH₃)₃ | 4.42 |
| 7 | O | I | H | phenyl (*,#) | CH(CH₃)CH₂C(CH₃)₃ | 4.16 |
| 8 | S | I | H | phenyl (*,#) | 4-Cl-phenyl | 3.93 |
| 9 | S | I | H | phenyl (*,#) | 3-F, 4-Cl-phenyl | 3.82 |
| 10 | O | I | H | phenyl (*,#) | 3,4-diCl-phenyl | 3.89 |
| 11 | O | I | H | phenyl (*,#) | 4-Cl-phenyl | 3.62 |

TABLE 1-continued
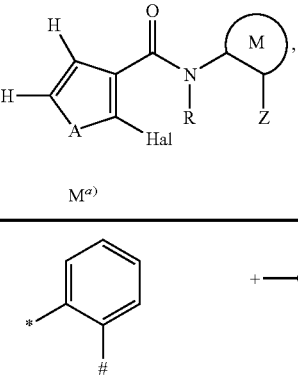
(I)
| No. | A | Hal | R | M[a] | Z[b] | logP |
|---|---|---|---|---|---|---|
| 12 | S | I | H | 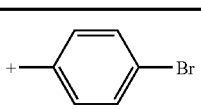 | 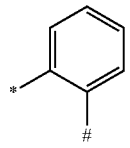 | 3.94 |
| 13 | S | I | H | 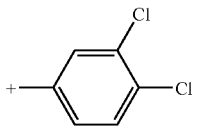 | 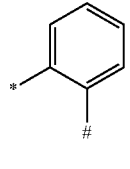 | 4.11 |
| 14 | S | I | H | 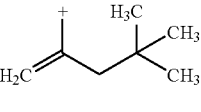 | 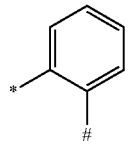 | 4.78 |
| 15 | O | I | H | 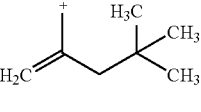 | 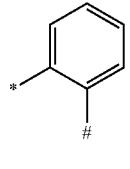 | 4.49 |
| 16 | O | I | H | 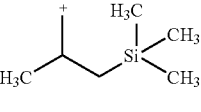 | 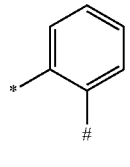 | 4.45 |
| 17 | S | I | H | 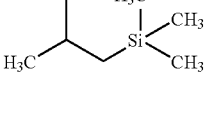 | 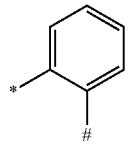 | 4.69 |
| 18 | S | I | H | 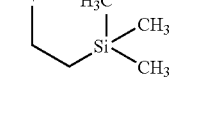 | 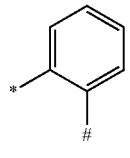 | 4.43 |
| 19 | S | I | H | 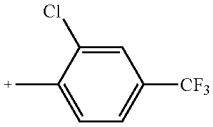 | | 4.18 |

TABLE 1-continued (I)

| No. | A | Hal | R | M[a] | Z[b] | logP |
|---|---|---|---|---|---|---|
| 20 | S | I | H | phenyl (*,#) | CH2CH2C(CH3)2CH3 | 4.17 |
| 21 | S | I | H | phenyl (*,#) | 2-Cl-4-Br-phenyl | 4.28 |
| 22 | S | I | H | phenyl (*,#) | 3-F-4-Br-phenyl | 3.89 |
| 23 | S | I | H | phenyl (*,#) | 2,3-diCl-phenyl | 4.01 |
| 24 | S | I | H | 4-F-phenyl (*,#) | 3,4-diCl-phenyl | 4.13 |
| 25 | S | I | H | phenyl (*,#) | 3-F-4-CH3-phenyl | 3.89 |
| 26 | S | I | H | phenyl (*,#) | 4-CF3-phenyl | 3.89 |
| 27 | S | Br | H | phenyl (*,#) | CH(CH3)CH2CH(CH3)2 | 4.24 |

TABLE 1-continued (I)

| No. | A | Hal | R | M$^{a)}$ | Z$^{b)}$ | logP |
|-----|---|-----|---|----------|----------|------|
| 28 | S | Br | H | phenyl (*,#) | 2,4,4-trimethylpentan-2-yl | 4.51 |
| 29 | S | Br | H | phenyl (*,#) | 4-Cl-phenyl | 3.99 |
| 30 | S | Br | H | phenyl (*,#) | 3,4-diCl-phenyl | 4.25 |
| 31 | S | Br | H | phenyl (*,#) | 3-F-4-Cl-phenyl | 3.91 |
| 32 | S | I | H | phenyl (*,#) | 3-Cl-4-Br-phenyl | 4.21 |
| 33 | S | I | H | phenyl (*,#) | 2-F-3-Cl-phenyl | 3.67 |
| 34 | S | I | H | pyridyl (*,#) | 3,4-diCl-phenyl | 2.20 |
| 35 | S | I | H | 4-F-phenyl (*,#) | 2-F-3-Cl-phenyl | 3.69 |

TABLE 1-continued (I)

| No. | A | Hal | R | M<sup>a)</sup> | Z<sup>b)</sup> | logP |
|-----|---|-----|---|----------------|----------------|------|
| 36 | S | I | H | 2,5-F-phenyl (*,#) | CH₂-C(CH₃)H-CH₂-Si(CH₃)₃ | 4.67 |
| 37 | S | I | H | 2,5-F-phenyl (*,#) | CH₂CH₂C(CH₃)₃ | 4.16 |
| 38 | S | I | H | phenyl (*,#) | 3-Cl-4-F-phenyl | 3.79 |
| 39 | S | I | H | 1,1,3-trimethyl-indanyl | | 4.09 |
| 40 | S | I | H | phenyl (*,#) | 2-F-phenyl-CH=N-OCH₃ | 3.79 |
| 41 | S | I | H | 2,4-F-phenyl (*,#) | CH(CH₃)CH₂CH(CH₃)₂ | 4.17 |
| 42 | S | I | H | thienyl (*,#) | CH₂CH₂C(CH₃)₃ | 4.44 |
| 43 | S | I | H | thienyl (*,#) | CH(CH₃)CH₂CH(CH₃)₂ | 4.22 |

TABLE 1-continued

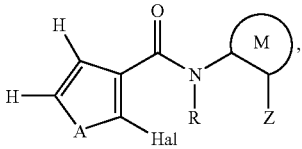

(I)

| No. | A | Hal | R | M[a)] | Z[b)] | logP |
|---|---|---|---|---|---|---|
| 44 | S | Br | H | 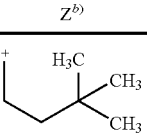 | 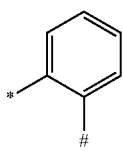 | 4.30 |
| 45 | S | Br | H | 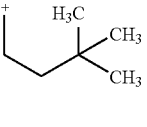 | 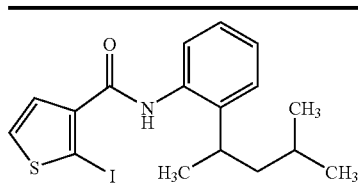 | 4.30 |

[a)]The bond marked "*" is attached to the amide, the bond marked "#" is attached to the radical Z.
[b)]The bond marked "+" is attached to the radical M.

The logP values given were determined in accordance with EEC Directive 79/831 Annex V.A8 by HPLC (High Performance Liquid Chromatography) on a reverse-phase column (C 18). Temperature: 43° C.

Mobile phases for the determination in the acidic range (pH 2.3): 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known logP values (determination of logP values by retention times using linear interpolation between two successive alkanones).

The lambda-max values were determined in the maxima of the chromatographic signals using the UV spectra from 200 nm to 400 nm.

USE EXAMPLES

Example A

| Sphaerotheca test (cucumber)/protective | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

TABLE A

Sphaerotheca test (cucumber)/protective

| Active compound according to the invention | Application rate of active compound in g/ha | Efficacy in % |
|---|---|---|
| 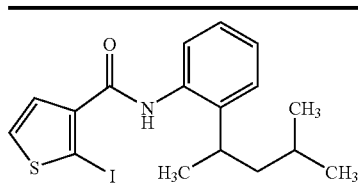 | 100 | 98 |

TABLE A-continued

Sphaerotheca test (cucumber)/protective

| Active compound according to the invention | Application rate of active compound in g/ha | Efficacy in % |
|---|---|---|
| [structure: 2-iodo-furan-3-carboxamide N-(2-(3,3-dimethylbutan-2-yl)phenyl)] | 100 | 98 |
| [structure: 2-iodo-thiophene-3-carboxamide N-(2-(3,3-dimethylbutan-2-yl)phenyl)] | 100 | 100 |
| [structure: 2-iodo-thiophene-3-carboxamide N-(2'-chloro-4'-trifluoromethylbiphenyl-2-yl)] | 100 | 100 |
| [structure: 2-iodo-thiophene-3-carboxamide N-(3-(3,4-dichlorophenyl)pyridin-4-yl)] | 100 | 100 |
| [structure: 2-iodo-thiophene-3-carboxamide N-(4'-bromo-2'-chlorobiphenyl-2-yl)] | 100 | 100 |
| [structure: 2-iodo-thiophene-3-carboxamide N-(4'-bromo-3'-fluorobiphenyl-2-yl)] | 100 | 100 |

TABLE A-continued

Sphaerotheca test (cucumber)/protective

| Active compound according to the invention | Application rate of active compound in g/ha | Efficacy in % |
|---|---|---|
| (structure) | 100 | 100 |
| (structure) | 100 | 100 |
| (structure) | 100 | 100 |
| (structure) | 100 | 100 |
| (structure) | 100 | 100 |
| (structure) | 100 | 100 |

TABLE A-continued

*Sphaerotheca* test (cucumber)/protective

| Active compound according to the invention | Application rate of active compound in g/ha | Efficacy in % |
|---|---|---|
| (2-iodofuran-3-carboxamide, N-(4'-bromobiphenyl-2-yl)) | 100 | 100 |
| (2-iodofuran-3-carboxamide, N-(3',4'-dichlorobiphenyl-2-yl)) | 100 | 100 |
| (2-iodofuran-3-carboxamide, N-(4'-chloro-3'-fluorobiphenyl-2-yl)) | 100 | 98 |
| (2-iodothiophene-3-carboxamide, N-(4'-chlorobiphenyl-2-yl)) | 100 | 95 |
| (2-iodothiophene-3-carboxamide, N-(4'-bromobiphenyl-2-yl)) | 100 | 100 |

TABLE A-continued
Sphaerotheca test (cucumber)/protective
| Active compound according to the invention | Application rate of active compound in g/ha | Efficacy in % |
|---|---|---|
| 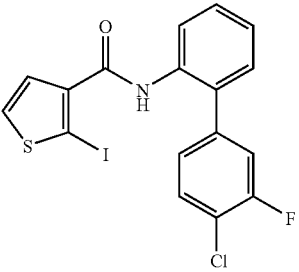 | 100 | 98 |
| 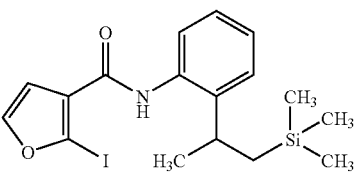 | 100 | 100 |
| 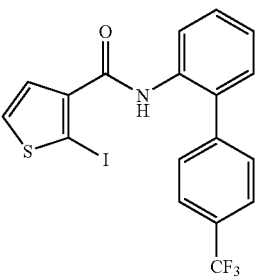 | 100 | 93 |
| 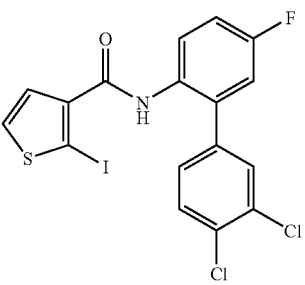 | 100 | 100 |
| 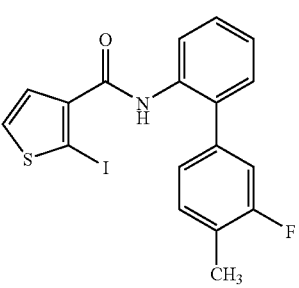 | 100 | 100 |
| 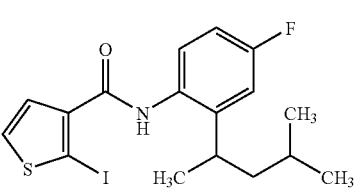 | 100 | 97 |

TABLE A-continued

Sphaerotheca test (cucumber)/protective

| Active compound according to the invention | Application rate of active compound in g/ha | Efficacy in % |
|---|---|---|
| (structure: 2-iodo-thiophene-3-carboxamide N-linked to biphenyl with F and CH=N-OCH3 substituents) | 100 | 98 |
| (structure: 2-iodo-thiophene-3-carboxamide N-linked to 2-(1,3-dimethylbutyl)thiophen-3-yl) | 100 | 92 |
| (structure: 2-bromo-thiophene-3-carboxamide N-linked to 2-(1,3-dimethylbutyl)phenyl) | 100 | 100 |
| (structure: 2-bromo-thiophene-3-carboxamide N-linked to 2-(1,3,3-trimethylbutyl)phenyl) | 100 | 97 |
| (structure: 2-bromo-thiophene-3-carboxamide N-linked to 4'-chlorobiphenyl-2-yl) | 100 | 100 |

TABLE A-continued

Sphaerotheca test (cucumber)/protective

| Active compound according to the invention | Application rate of active compound in g/ha | Efficacy in % |
|---|---|---|
| [structure: thiophene-Br with C(O)NH-biphenyl-3,4-diCl] | 100 | 100 |
| [structure: thiophene-Br with C(O)NH-biphenyl-3-Cl-4-F] | 100 | 100 |
| [structure: thiophene-I with C(O)NH-biphenyl-3-Cl-4-F] | 100 | 100 |
| [structure: thiophene-I with C(O)NH-thiophene-CH$_2$CH$_2$Si(CH$_3$)$_3$] | 100 | 100 |

Example B

| Venturia test (apple)/protective | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, one part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE B

*Venturia* test (apple)/protective

| Active compound according to the invention | Application rate of active compound in g/ha | Efficacy in % |
|---|---|---|
| (2-iodothiophene-3-carboxamide with 2-(2,4-dimethylpentan-3-yl)phenyl) | 100 | 100 |
| (2-iodofuran-3-carboxamide with 2-(3,3-dimethylbutan-2-yl)phenyl) | 100 | 94 |
| (2-iodothiophene-3-carboxamide with 2-(3,3-dimethylbutan-2-yl)phenyl) | 100 | 100 |
| (2-iodothiophene-3-carboxamide with 2-(2-(trimethylsilyl)ethyl)phenyl) | 100 | 100 |
| (2-iodothiophene-3-carboxamide with 2'-chloro-4'-(trifluoromethyl)biphenyl-2-yl) | 100 | 97 |
| (2-iodothiophene-3-carboxamide with 3-(3,4-dichlorophenyl)pyridin-4-yl) | 100 | 98 |

TABLE B-continued

*Venturia* test (apple)/protective

| Active compound according to the invention | Application rate of active compound in g/ha | Efficacy in % |
|---|---|---|
| 2-iodo-thiophene-3-carboxamide of 2'-chloro-4'-bromo-biphenyl-2-yl | 100 | 100 |
| 2-iodo-thiophene-3-carboxamide of 3'-fluoro-4'-bromo-biphenyl-2-yl | 100 | 100 |
| 2-iodo-thiophene-3-carboxamide of 3'-chloro-4'-bromo-biphenyl-2-yl | 100 | 100 |
| 2-iodo-thiophene-3-carboxamide of 2',3'-dichloro-biphenyl-2-yl | 100 | 98 |
| 2-iodo-thiophene-3-carboxamide of 2'-fluoro-3'-chloro-biphenyl-2-yl | 100 | 89 |

TABLE B-continued

*Venturia* test (apple)/protective

| Active compound according to the invention | Application rate of active compound in g/ha | Efficacy in % |
|---|---|---|
| [structure: 2-iodothiophene-3-carboxamide with 5-fluoro-2'-fluoro-3'-chlorobiphenyl] | 100 | 100 |
| [structure: 2-iodothiophene-3-carboxamide with 4-fluoro-2-(3,3-dimethylbutyl)phenyl] | 100 | 100 |
| [structure: 2-iodofuran-3-carboxamide with 4'-chlorobiphenyl] | 100 | 100 |
| [structure: 2-iodofuran-3-carboxamide with 4'-bromobiphenyl] | 100 | 100 |
| [structure: 2-iodofuran-3-carboxamide with 3',4'-dichlorobiphenyl] | 100 | 99 |

TABLE B-continued

*Venturia* test (apple)/protective

| Active compound according to the invention | Application rate of active compound in g/ha | Efficacy in % |
|---|---|---|
| (2-iodo-furan-3-carboxamide with 4'-chloro-3'-fluoro-biphenyl-2-yl) | 100 | 100 |
| (2-iodo-thiophene-3-carboxamide with 4'-chloro-biphenyl-2-yl) | 100 | 100 |
| (2-iodo-thiophene-3-carboxamide with 4'-bromo-biphenyl-2-yl) | 100 | 91 |
| (2-iodo-thiophene-3-carboxamide with 3',4'-dichloro-biphenyl-2-yl) | 100 | 100 |
| (2-iodo-thiophene-3-carboxamide with 4'-chloro-3'-fluoro-biphenyl-2-yl) | 100 | 100 |

TABLE B-continued
*Venturia* test (apple)/protective
| Active compound according to the invention | Application rate of active compound in g/ha | Efficacy in % |
|---|---|---|
| 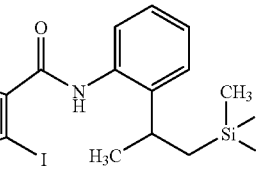 | 100 | 99 |
| 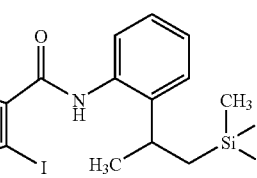 | 100 | 100 |
| 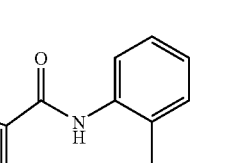 | 100 | 99 |
| 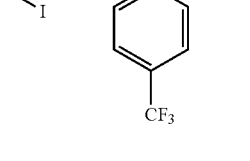 | 100 | 100 |
| 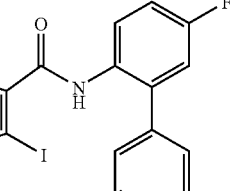 | 100 | 100 |
| 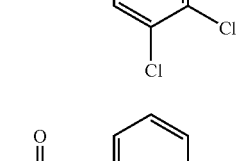 | 100 | 100 |

TABLE B-continued
Venturia test (apple)/protective
| Active compound according to the invention | Application rate of active compound in g/ha | Efficacy in % |
|---|---|---|
| 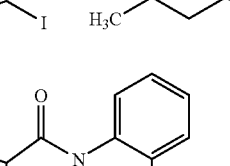 | 100 | 100 |
| 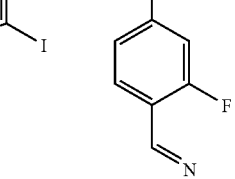 | 100 | 100 |
| 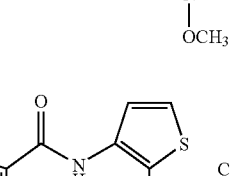 | 100 | 100 |
| 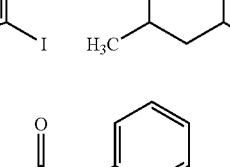 | 100 | 100 |
| 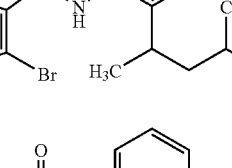 | 100 | 98 |
| 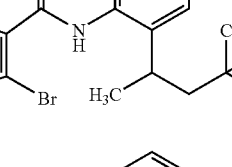 | 100 | 100 |

TABLE B-continued

Venturia test (apple)/protective

| Active compound according to the invention | Application rate of active compound in g/ha | Efficacy in % |
|---|---|---|
| 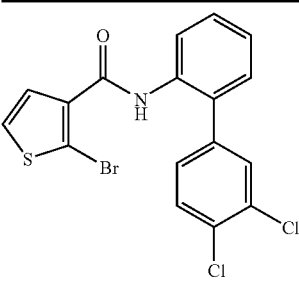 | 100 | 100 |
| 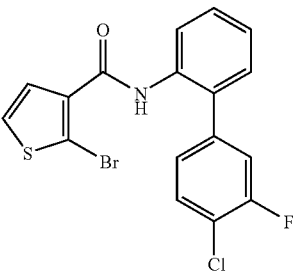 | 100 | 100 |
| 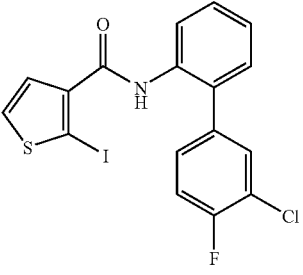 | 100 | 100 |
| 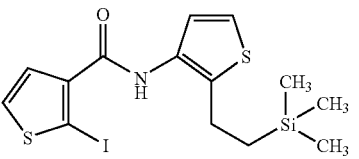 | 100 | 100 |

Example C

Botrytis test (bean)/protective

| | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound was mixed with the stated amounts of solvent and emulsifier, and the concentrate was diluted with water to the desired concentration.

To test for protective activity, young plants are sprayed with the preparation of active compound at the stated application rate. After the spray coating has dried on, 2 small pieces of agar colonized by Botrytis cinerea are placed onto each leaf. The inoculated plants are placed in a dark chamber at about 20° C. and 100% relative atmospheric humidity.

The size of the infected areas on the leaves is evaluated 2 days after the inoculation. 0% means an efficacy which corresponds to that of the control, whereas an efficacy of 100% means that no infection is observed.

TABLE C

*Botrytis* test (bean)/protective

| Active compound according to the invention | Application rate of active compound in g/ha | Efficacy in % |
|---|---|---|
| [structure: 2-iodo-thiophene-3-carboxamide with N-(2-(2-methylpentan-3-yl)phenyl)] | 500 | 100 |
| [structure: 2-iodo-furan-3-carboxamide with N-(2-(2-methylpentan-3-yl)phenyl)] | 500 | 99 |
| [structure: 2-iodo-furan-3-carboxamide with N-(2-(3,3-dimethylbutan-2-yl)phenyl)] | 500 | 100 |
| [structure: 2-iodo-thiophene-3-carboxamide with N-(2-(3,3-dimethylbutan-2-yl)phenyl)] | 500 | 100 |
| [structure: 2-iodo-thiophene-3-carboxamide with N-(2-(2-(trimethylsilyl)ethyl)phenyl)] | 500 | 100 |
| [structure: 2-iodo-thiophene-3-carboxamide with N-(2'-chloro-4'-(trifluoromethyl)biphenyl-2-yl)] | 500 | 100 |
| [structure: 2-iodo-thiophene-3-carboxamide with N-(3-(3,4-dichlorophenyl)pyridin-4-yl)] | 500 | 100 |

TABLE C-continued

*Botrytis* test (bean)/protective

| Active compound according to the invention | Application rate of active compound in g/ha | Efficacy in % |
|---|---|---|
| 2-iodothiophene-3-carboxamide of 2'-chloro-4'-bromobiphenyl-2-yl | 500 | 100 |
| 2-iodothiophene-3-carboxamide of 3'-fluoro-4'-bromobiphenyl-2-yl | 500 | 100 |
| 2-iodothiophene-3-carboxamide of 3'-chloro-4'-bromobiphenyl-2-yl | 500 | 100 |
| 2-iodothiophene-3-carboxamide of 2',3'-dichlorobiphenyl-2-yl | 500 | 100 |
| 2-iodothiophene-3-carboxamide of 2'-fluoro-3'-chlorobiphenyl-2-yl | 500 | 100 |

TABLE C-continued
*Botrytis* test (bean)/protective
| Active compound according to the invention | Application rate of active compound in g/ha | Efficacy in % |
|---|---|---|
| 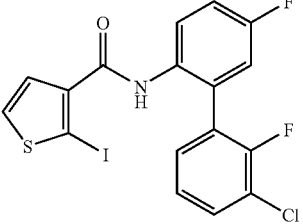 | 500 | 100 |
| 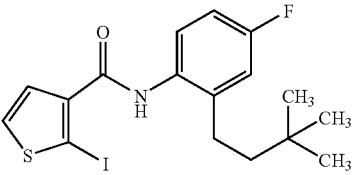 | 500 | 100 |
| 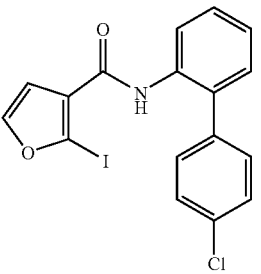 | 500 | 100 |
| 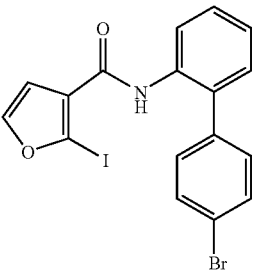 | 500 | 100 |
| 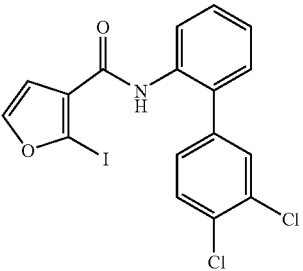 | 500 | 100 |

TABLE C-continued

Botrytis test (bean)/protective

| Active compound according to the invention | Application rate of active compound in g/ha | Efficacy in % |
|---|---|---|
| 2-iodo-furan-3-carboxamide with 4'-chloro-3'-fluoro-biphenyl-2-yl | 500 | 100 |
| 2-iodo-thiophene-3-carboxamide with 4'-chloro-biphenyl-2-yl | 500 | 100 |
| 2-iodo-thiophene-3-carboxamide with 4'-bromo-biphenyl-2-yl | 500 | 100 |
| 2-iodo-thiophene-3-carboxamide with 3',4'-dichloro-biphenyl-2-yl | 500 | 100 |
| 2-iodo-thiophene-3-carboxamide with 4'-chloro-3'-fluoro-biphenyl-2-yl | 500 | 100 |

TABLE C-continued

Botrytis test (bean)/protective

| Active compound according to the invention | Application rate of active compound in g/ha | Efficacy in % |
|---|---|---|
| (structure: 2-iodo-furan-3-carboxamide with N-[2-(1-methyl-2-(trimethylsilyl)ethyl)phenyl]) | 500 | 100 |
| (structure: 2-iodo-thiophene-3-carboxamide with N-[2-(1-methyl-2-(trimethylsilyl)ethyl)phenyl]) | 500 | 100 |
| (structure: 2-iodo-thiophene-3-carboxamide with N-[2-(4'-trifluoromethylbiphenyl-2-yl)]) | 500 | 100 |
| (structure: 2-iodo-thiophene-3-carboxamide with N-[4-fluoro-2-(3,4-dichlorophenyl)phenyl]) | 500 | 100 |
| (structure: 2-iodo-thiophene-3-carboxamide with N-[2-(3-fluoro-4-methylphenyl)phenyl]) | 500 | 100 |
| (structure: 2-iodo-thiophene-3-carboxamide with N-[1,3,3-trimethylindan-4-yl]) | 500 | 100 |

TABLE C-continued

*Botrytis* test (bean)/protective

| Active compound according to the invention | Application rate of active compound in g/ha | Efficacy in % |
|---|---|---|
| 2-iodo-N-(4-fluoro-2-(2-methyl-4-methylpentan-2-yl)phenyl)thiophene-3-carboxamide structure | 500 | 100 |
| 2-iodo-N-(2'-fluoro-4'-((methoxyimino)methyl)biphenyl-2-yl)thiophene-3-carboxamide structure | 500 | 100 |
| 2-iodo-N-(2-(4-methylpentan-2-yl)thiophen-3-yl)thiophene-3-carboxamide structure | 500 | 100 |
| 2-bromo-N-(2-(4-methylpentan-2-yl)phenyl)thiophene-3-carboxamide structure | 500 | 100 |
| 2-bromo-N-(2-(3,3-dimethylbutan-2-yl)phenyl)thiophene-3-carboxamide structure | 500 | 100 |
| 2-bromo-N-(4'-chlorobiphenyl-2-yl)thiophene-3-carboxamide structure | 500 | 100 |

TABLE C-continued

Botrytis test (bean)/protective

| Active compound according to the invention | Application rate of active compound in g/ha | Efficacy in % |
|---|---|---|
| 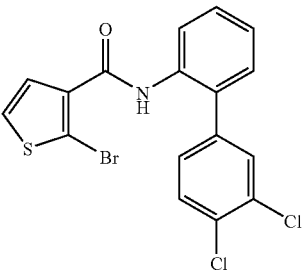 | 500 | 100 |
| 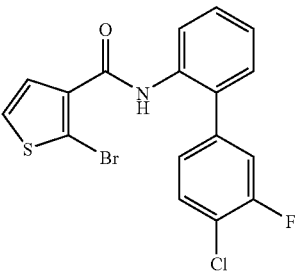 | 500 | 100 |
| 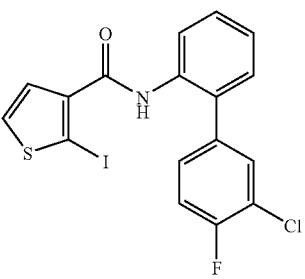 | 500 | 99 |
| 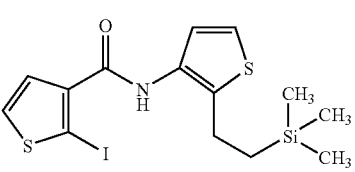 | 500 | 100 |

Example D

Puccinia test (wheat)/protective

| | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

TABLE D

*Puccinia* test (wheat)/protective

| Active compound according to the invention | Application rate of active compound in g/ha | Efficacy in % |
|---|---|---|
| 2-iodo-thiophene-3-carboxamide with N-[2-(1,3-dimethylbutyl)phenyl] group | 500 | 100 |
| 2-iodo-furan-3-carboxamide with N-[2-(1,3-dimethylbutyl)phenyl] group | 500 | 100 |
| 2-iodo-thiophene-3-carboxamide with N-[2-(2-(trimethylsilyl)ethyl)phenyl] group | 500 | 97 |
| 2-iodo-thiophene-3-carboxamide with N-[2-(3,3-dimethylbutyl)phenyl] group | 500 | 97 |
| 2-iodo-thiophene-3-carboxamide with N-(4'-bromo-3'-fluorobiphenyl-2-yl) group | 500 | 100 |
| 2-iodo-thiophene-3-carboxamide with N-(4'-bromo-3'-chlorobiphenyl-2-yl) group | 500 | 100 |
| 2-iodo-thiophene-3-carboxamide with N-[4-fluoro-2-(3,3-dimethylbutyl)phenyl] group | 500 | 100 |

TABLE D-continued

*Puccinia* test (wheat)/protective

| Active compound according to the invention | Application rate of active compound in g/ha | Efficacy in % |
|---|---|---|
| (2-iodofuran-3-carboxamide of 4'-chloro-biphenyl-2-yl) | 500 | 100 |
| (2-iodofuran-3-carboxamide of 4'-bromo-biphenyl-2-yl) | 500 | 100 |
| (2-iodofuran-3-carboxamide of N-[2-(2,4,4-trimethylpentan-2-yl... ]) | 500 | 100 |
| (2-iodofuran-3-carboxamide of 4'-chloro-3'-fluoro-biphenyl-2-yl) | 500 | 100 |
| (2-iodothiophene-3-carboxamide of 3',4'-dichloro-biphenyl-2-yl) | 500 | 100 |
| (2-iodothiophene-3-carboxamide aniline derivative) | 500 | 100 |

TABLE D-continued

*Puccinia* test (wheat)/protective

| Active compound according to the invention | Application rate of active compound in g/ha | Efficacy in % |
|---|---|---|
| (structure) | 500 | 93 |
| (structure) | 500 | 94 |
| (structure) | 500 | 100 |
| (structure) | 500 | 100 |
| (structure) | 500 | 100 |
| (structure) | 500 | 100 |
| (structure) | 500 | 100 |

TABLE D-continued

*Puccinia* test (wheat)/protective

| Active compound according to the invention | Application rate of active compound in g/ha | Efficacy in % |
|---|---|---|
| [structure: 2-iodo-thiophene-3-carboxamide with 2-biphenyl bearing 3-fluoro-4-(CH=N-OCH₃) substituent] | 500 | 100 |
| [structure: 2-iodo-thiophene-3-carboxamide N-linked to 2-(2,4-dimethylpent-3-yl)thiophen-3-yl] | 500 | 100 |
| [structure: 2-bromo-thiophene-3-carboxamide N-linked to 2-(2,4-dimethylpent-3-yl)phenyl] | 500 | 100 |
| [structure: 2-bromo-thiophene-3-carboxamide N-linked to 2-(2,3,3-trimethylbut-2-yl... 2-methyl-pentyl)phenyl] | 500 | 100 |
| [structure: 2-bromo-thiophene-3-carboxamide with 2-biphenyl bearing 3,4-dichloro substituents] | 500 | 100 |
| [structure: 2-bromo-thiophene-3-carboxamide with 2-biphenyl bearing 3-fluoro-4-chloro substituents] | 500 | 100 |

TABLE D-continued

Puccinia test (wheat)/protective

| Active compound according to the invention | Application rate of active compound in g/ha | Efficacy in % |
|---|---|---|
| [structure: thiophene-carboxamide with 2-I, N-H linked to biphenyl bearing 3-Cl, 4-F] | 500 | 100 |
| [structure: thiophene-carboxamide with 2-I, N-H linked to 4-fluorophenyl bearing CH(CH3)CH2-Si(CH3)3 group] | 500 | 100 |

Example E

Alternaria test (tomato)/proctective

| | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. One day after the treatment, the plants are inoculated with a spore suspension of *Alternaria solani* and then remain at 100% relative humidity and at 20° C. for 24 hours. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

TABLE E

Alternaria test (tomato)/protective

| Active compound according to the invention | Application rate of active compound in g/ha | Efficacy in % |
|---|---|---|
| [structure: thiophene-carboxamide with 2-I, N-H linked to phenyl bearing CH2C(CH3)3 group] | 750 | 94 |
| [structure: thiophene-carboxamide with 2-I, N-H linked to phenyl bearing CH(CH3)CH2CH(CH3)2 group] | 750 | 100 |

TABLE E-continued

Alternaria test (tomato)/protective

| Active compound according to the invention | Application rate of active compound in g/ha | Efficacy in % |
|---|---|---|
| 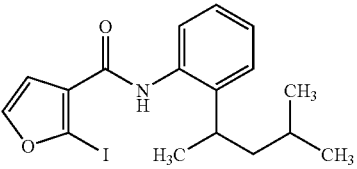 | 750 | 94 |

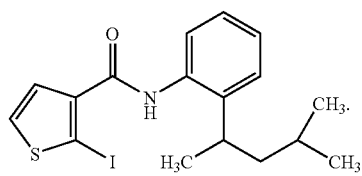

The invention claimed is:
1. 2-Halofuryl/thienyl-3-carboxamides of the formula (I)

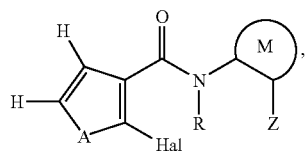

in which
A represents O (oxygen) or S (sulphur),
Hal represents halogen,
R represents hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^1$, —CONR$^2$R$^3$ or —CH$_2$NR$^4$R$^5$,
$R^1$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^2$ and $R^3$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^2$ and $R^3$ furthermore together with the nitrogen atom to which they are attached form a saturated heterocycle having 5 to 8 ring atoms which is optionally mono- or polysubstituted by identical or different substituents selected from the group consisting of halogen and $C_1$-$C_4$-alkyl, where the heterocycle optionally contains one or two further non-adjacent heteroatoms selected from the group consisting of oxygen, sulphur and NR$^6$,
$R^4$ and $R^5$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms,
$R^4$ and $R^5$ furthermore together with the nitrogen atom to which they are attached form a saturated heterocycle having 5 to 8 ring atoms which is optionally mono- or polysubstituted by identical or different substituents selected from the group consisting of halogen and $C_1$-$C_4$-alkyl, where the heterocycle optionally contains 1 or 2 further non-adjacent heteroatoms selected from the group consisting of oxygen, sulphur and NR$^6$,
$R^6$ represents hydrogen or $C_1$-$C_6$-alkyl,
M represents a phenyl which is monosubstituted by $R^7$,
$R^7$ represents hydrogen, fluorine, chlorine, methyl, isopropyl, methylthio or trifluoromethyl,
Z represents $Z^1$, $Z^2$, $Z^3$ or $Z^4$, in which
$Z^1$ represents phenyl which is optionally mono- to pentasubstituted by identical or different substituents $W^1$,
$W^1$ represents halogen, cyano, nitro, amino, hydroxyl, formyl, carboxy, carbamoyl, thiocarbamoyl;
in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;
in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;
in each case straight-chain or branched haloalkenyl or haloalkenyloxy having in each case 2 to 6 carbon atoms and 1 to 11 identical or different halogen atoms;
in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy having 1 to 6 carbon atoms in the respective hydrocarbon chains, alkenylcarbonyl or alkynylcarbonyl having 2 to 6 carbon atoms in the respective hydrocarbon chains;
cycloalkyl or cycloalkyloxy having in each case 3 to 6 carbon atoms;
doubly attached alkylene having 3 or 4 carbon atoms, oxyalkylene having 2 or 3 carbon atoms, each of which is optionally mono- to tetrasubstituted by identical or different substituents selected from the group consisting of fluorine, chlorine, oxo, methyl, trifluoromethyl and ethyl;

$Z^2$ represents bicycloalkyl or cycloalkyl which is optionally mono- or polysubstituted by identical or different substituents, $Z^3$ represents unsubstituted $C_2$-$C_{20}$-alkyl or represents $C_1$-$C_{20}$-alkyl which is mono- or polysubstituted by identical or different substituents selected from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and $C_3$-$C_6$-cycloalkyl, where the cycloalkyl moiety is optionally mono- or polysubstituted by identical or different substituents selected from the group consisting of halogen and $C_1$-$C_4$-alkyl, $Z^4$ represents $C_2$-$C_{20}$-alkenyl or $C_2$-$C_{20}$-alkynyl, each of which is optionally mono- or polysubstituted by identical or different substituents selected from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halo-dialkylamino, —$SiR^8R^9R^{10}$ and $C_3$-$C_6$-cycloalkyl, where the cycloalkyl moiety is optionally mono- or polysubstituted by identical or different substituents selected from the group consisting of halogen and $C_1$-$C_4$-alkyl, $R^8$ and $R^9$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl, $R^{10}$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or represents in each case optionally substituted phenyl or phenylalkyl.

2. 2-Halofuryl/thienyl-3-carboxamides of the formula (I) according to claim 1 in which A represents O (oxygen) or S (sulphur), Hal represents fluorine, chlorine, bromine or iodine, R represents hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms; ($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms, or —C(=O)C(=O)$R^1$, —CONR$^2$R$^3$ or —CH$_2$NR$^4$R$^5$, $R^1$ represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, ($C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms, $R^2$ and $R^3$ independently of one another each represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms, $R^2$ and $R^3$ furthermore together with the nitrogen atom to which they are attached form a saturated heterocycle having 5 or 6 ring atoms which is optionally mono- to tetrasubstituted by identical or different substituents selected from the group consisting of halogen and $C_1$-$C_4$-alkyl, where the heterocycle optionally contains 1 or 2 further non-adjacent heteroatoms selected from the group consisting of oxygen, sulphur and NR$^6$, $R^4$ and $R^5$ independently of one another represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms, $R^4$ and $R^5$ furthermore together with the nitrogen atom to which they are attached form a saturated heterocycle having 5 or 6 ring atoms which is optionally mono- or polysubstituted by identical or different substituents selected from the group consisting of halogen and $C_1$-$C_4$-alkyl, where the heterocycle optionally contains 1 or 2 further non-adjacent heteroatoms selected from the group consisting of oxygen, sulphur and NR$^6$, $R^6$ represents hydrogen or $C_1$-$C_4$-alkyl, M represents

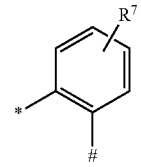

where the bond marked "*" is attached to the amide and the bond marked "#" is attached to the radical Z, $R^7$ represents hydrogen, fluorine, chlorine, methyl, isopropyl, methylthio or trifluoromethyl, Z represents $Z^1$, $Z^2$, $Z^3$ or $Z^4$, where $Z^1$ represents phenyl which is optionally mono- to pentasubstituted by identical or different substituents $W^1$, $W^1$ represents halogen, cyano, nitro, amino, hydroxyl, formyl, carboxy, carbamoyl, thiocarbamoyl;

in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkylsulphinyl or haloalkylsulphonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy having 1 to 6 carbon atoms in the respective hydrocarbon chains, alkenylcarbonyl or alkynylcarbonyl having 2 to 6 carbon atoms in the respective hydrocarbon chains;

cycloalkyl or cycloalkyloxy having in each case 3 to 6 carbon atoms;

doubly attached alkylene having 3 or 4 carbon atoms, oxyalkylene having 2 or 3 carbon atoms, each of which is optionally mono- to tetrasubstituted by identical or different substituents selected from the group consisting of fluorine, chlorine, oxo, methyl, trifluoromethyl and ethyl;

$Z^2$ represents cycloalkyl or bicycloalkyl having in each case 3 to 10 carbon atoms and being in each case optionally mono- to tetrasubstituted by identical or different substituents selected from the group consisting of halogen and/or $C_1$-$C_4$-alkyl, $Z^3$ represents unsubstituted $C_2$-$C_{20}$-alkyl or $C_1$-$C_{20}$-alkyl which is mono- or polysubstituted by identical or different substituents from the group consisting of fluorine, chlorine, bromine, iodine, $C_1$-$C_6$-alkylthio, $C_1$-$C_6$-alkylsulphinyl, $C_1$-$C_6$-alkyl-sulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-cycloalkyl, where the cycloalkyl moiety is optionally mono- to tetrasubstituted by identical or different substituents selected from the group consisting of fluorine, chlorine, bromine, iodine, $C_1$-$C_4$-alkyl and $C_1$-$C_4$-haloalkyl, $Z^4$ represents $C_2$-$C_{20}$-alkenyl or $C_2$-$C_{20}$-alkynyl, each of which is optionally mono- or polysubstituted by identical or different substituents selected from the group consisting of fluorine, chlorine, bromine, iodine, $C_1$-$C_6$-alkylthio, $C_1$-$C_6$-alkylsulphinyl, $C_1$-$C_6$-alkylsulphonyl, $C_1$-$C_6$-alkoxy, $C_1$-$C_6$-alkylamino, di($C_1$-$C_6$-alkyl)amino, $C_1$-$C_6$-haloalkylthio, $C_1$-$C_6$-haloalkylsulphinyl, $C_1$-$C_6$-haloalkylsulphonyl, $C_1$-$C_6$-haloalkoxy, $C_1$-$C_6$-haloalkylamino, halo-di($C_1$-$C_6$-alkyl)amino, —$SiR^8R^9R^{10}$ and $C_3$-$C_6$-cycloalkyl, where the cycloalkyl moiety is optionally mono- to tetrasubstituted by identical or different substituents from the group consisting of fluorine, chlorine, bromine, iodine, $C_1$-$C_4$-alkyl and $C_1$-$C_4$-haloalkyl, $R^8$ and $R^9$ independently of one another represent $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl, $R^{10}$ represents $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

3. Process for preparing the 2-halofuryl/thienyl-3-carboxamides of the formula (I) according to claim 1, characterized in that a) carboxylic acid derivatives of the formula (II)

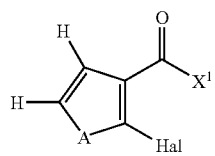

(II)

in which

A and Hal are as defined in claim 1 and $X^1$ represents halogen or hydroxyl are reacted with aniline derivatives of the formula (III)

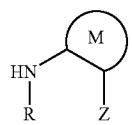

(III)

in which R, M and Z are as defined in claim 1, optionally in the presence of a catalyst, optionally in the presence of a condensing agent, optionally in the presence of an acid binder and optionally in the presence of a diluent, or b) halocarboxamides of the formula (IV)

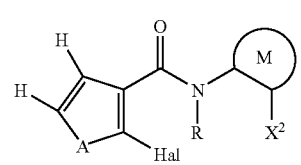

(IV)

in which

A, Hal, R and M are as defined in claim 1, $X^2$ represents bromine, iodine or trifluoromethylsulphonate, are reacted with boronic acid derivatives of the formula (V)

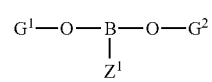

(V)

in which $Z^1$ is as defined in claim 1 and $G^1$ and $G^2$ each represent hydrogen or together represent tetramethylethylene, in the presence of a catalyst, optionally in the presence of an acid binder and optionally in the presence of a diluent, or c) boronic acid derivatives of the formula (VI)

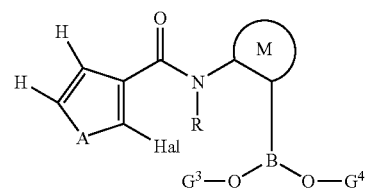

(VI)

in which

A, Hal, R and M are as defined in claim 1, $G^3$ and $G^4$ each represent hydrogen or together represent tetramethylethylene are reacted with phenyl derivatives of the formula (VII)

$X^3$-$Z^1$ (VII)

in which $Z^1$ is as defined in claim 1 and $X^3$ represents chlorine, bromine, iodine or trifluoromethylsulphonate, optionally in the presence of a catalyst, optionally in the presence of an acid binder and optionally in the presence of a diluent, or d) halocarboxamides of the formula (IV)

(IV)

in which

A, Hal, R and M are as defined in claim 1, $X^2$ represents bromine, iodine or trifluoromethylsulphonate, are reacted with phenyl derivatives of the formula (VII)

$$X^3-Z^1 \qquad (VII)$$

in which $Z^1$ is as defined in claim 1 and $X^3$ represents chlorine, bromine, iodine or trifluoromethylsulphonate, in the presence of a palladium or nickel catalyst and in the presence of 4,4,4',4',5,5,5'5'-octamethyl-2,2'-bis-1,3,2-dioxaborolane, optionally in the presence of an acid binder and optionally in the presence of a diluent, or e) 2-halofuryl/thienyl-3-carboxamides of the formula (I-a)

(I-a)

in which

A, Hal, R and M are as defined in claim 1, $X^4$ represents $C_2$-$C_{20}$-alkenyl or $C_2$-$C_{20}$-alkynyl which are in each case optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —SiR$^8$R$^9$R$^{10}$ and $C_3$-$C_6$-cycloalkyl, where the cycloalkyl moiety is optionally substituted by halogen and/or $C_1$-$C_4$ alkyl, are hydrogenated, optionally in the presence of a diluent and optionally in the presence of a catalyst, or f) hydroxyalkylcarboxamides of the formula (VIII)

(VIII)

in which

A, Hal, R and M are as defined in claim 1, $X^5$ represents $C_2$-$C_{20}$-hydroxyalkyl which is optionally additionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —SiR$^8$R$^9$R$^{10}$ and $C_3$-$C_6$-cycloalkyl, where the cycloalkyl moiety is optionally substituted by halogen and/or $C_1$-$C_4$-alkyl, are dehydrated, optionally in the presence of a diluent and optionally in the presence of an acid, or g) halocarboxamides of the formula (IV)

(IV)

in which

A, Hal, R and M are as defined in claim 1, $X^2$ represents bromine, iodine or trifluoromethylsulphonate, are reacted with an alkyne of the formula (IX)

$$HC\equiv\!\!\!\equiv\!\!\!-G^5 \qquad (IX)$$

in which $G^5$ represents $C_2$-$C_{18}$-alkyl which is optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —SiR$^8$R$^9$R$^{10}$ and $C_3$-$C_6$-cycloalkyl, where the cycloalkyl moiety is optionally substituted by halogen and/or $C_1$-$C_4$-alkyl, or an alkene of the formula (X)

(X)

in which $G^6$, $G^7$ and $G^8$ independently of one another each represent hydrogen or alkyl which is optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —SiR$^8$R$^9$R$^{10}$ and $C_3$-$C_6$-cycloalkyl, where the cycloalkyl moiety is optionally substituted by halogen and/or $C_1$-$C_4$-alkyl and the total number of carbon atoms of the open-chain molecular moiety (without substituents) does not exceed the number 20, optionally in the presence of a diluent, optionally in the presence of an acid binder and optionally in the presence of one or more catalysts, or h) ketones of the formula (XI)

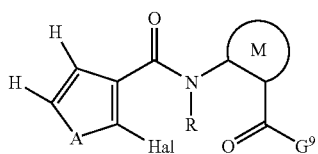

(XI)

in which

A, Hal, R and M are as defined in claim 1, $G^9$ represents hydrogen or $C_1$-$C_{18}$-alkyl which is optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and $C_3$-$C_6$-cycloalkyl, where the cycloalkyl moiety is optionally substituted by halogen and/or $C_1$-$C_4$-alkyl, are reacted with a phosphorus compound of the general formula (XII)

$G^{10}$-Px  (XII)

in which $G^{10}$ represents $C_1$-$C_{18}$-alkyl which is optionally mono- or polysubstituted by identical or different substituents from the group consisting of halogen, alkylthio, alkylsulphinyl, alkylsulphonyl, alkoxy, alkylamino, dialkylamino, haloalkylthio, haloalkylsulphinyl, haloalkylsulphonyl, haloalkoxy, haloalkylamino, halodialkylamino, —$SiR^8R^9R^{10}$ and $C_3$-$C_6$-cycloalkyl, where the cycloalkyl moiety is optionally substituted by halogen and/or $C_1$-$C_4$-alkyl, Px represents a grouping —$P^+(C_6H_5)_3Cl^-$, —$P^+(C_6H_5)_3Br^-$, —$P^+(C_6H_5)_3I^-$, —$P(=O)(OCH_3)_3$ or —$P(=O)(OCH_2H_5)_3$, optionally in the presence of a diluent, or i) 2-halofuryl/thienyl-3-carboxamides of the formula (I-b)

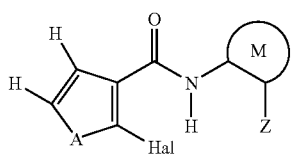

(I-b)

in which

A, Hal, R, M and Z are as defined in claim 1 are reacted with halides of the formula (XIII)

$R^a$—$X^6$  (XIII)

in which $R^a$ represents $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —$C(=O)C(=O)R^1$, —$CONR^2R^3$ or —$CH_2NR^4R^5$, $R^1$, $R^2$, $R^3$, $R^4$ and $R^5$ are as defined above, $X^6$ represents chlorine, bromine or iodine, in the presence of a base and in the presence of a diluent.

4. A composition comprising at least one 2-halofuryl/thienyl-3-carboxamide of the formula (I) according to claim 1, and one or more extenders and/or surfactants.

5. A method for controlling fungi and bacteria in crop protection, comprising applying at least one 2-halofuryl/thienyl-3-carboxamide of the formula (I) according to claim 1 to fungi, bacteria and/or their habitat.

6. A process for preparing a composition according to claim 4, comprising mixing at least one 2-halofuryl/thienyl-3-carboxamide of the formula (I) according to claim 1 with extenders and/or surfactants.

7. 2-Halofuryl/thienyl-3-carboxamides of the formula (I) according to claim 1, in which
R represents hydrogen, and
Z represents $Z^1$.

8. 2-Halofuryl/thienyl-3-carboxamides of the formula (I) according to claim 1, in which
R represents hydrogen, and
Z represents $Z^3$.

9. 2-Halofuryl/thienyl-3-carboxamides of the formula (I) according to claim 1, in which
R represents hydrogen, and
Z represents $Z^4$.

10. 2-Halofuryl/thienyl-3-carboxamides of the formula (I) according to claim 1, in which
R represents hydrogen,
$R^7$ represents hydrogen or fluorine, and
Z represents $Z^3$.

11. 2-Halofuryl/thienyl-3-carboxamides of the formula (I) according to claim 10, in which
$Z^3$ represents unsubstituted $C_2$-$C_{20}$-alkyl.

12. N-[2-(1,3-dimethylbutyl)phenyl]-2-iodothiophene-3-carboxamide: